United States Patent [19]
Ouellette

[11] Patent Number: 5,938,593
[45] Date of Patent: Aug. 17, 1999

[54] SKIN ANALYZER WITH SPEECH CAPABILITY

[75] Inventor: Loren R. Ouellette, Reno, Nev.

[73] Assignee: Microline Technologies, Inc., Reno, Nev.

[21] Appl. No.: 08/963,576

[22] Filed: Nov. 6, 1997

Related U.S. Application Data

[63] Continuation of application No. 08/615,395, Mar. 12, 1996, abandoned.

[51] Int. Cl.$^6$ ............................................. A61B 5/05
[52] U.S. Cl. ........................... 600/300; 600/547; 324/692
[58] Field of Search ................... 600/300, 309, 600/547, 345; 324/692, 694, 696, 722

[56] References Cited

U.S. PATENT DOCUMENTS

| | | | |
|---|---|---|---|
| D. 286,676 | 11/1986 | McJunkin | D24/17 |
| D. 286,921 | 11/1986 | Takigawa | D28/9 |
| D. 351,560 | 10/1994 | Schneider | D10/56 |
| 3,761,810 | 9/1973 | Fathauer | 324/61 R |
| 4,013,065 | 3/1977 | Copeland et al. | 128/2 R |
| 4,088,125 | 5/1978 | Forgione et al. | 128/2.1 Z |
| 4,096,852 | 6/1978 | Adams | 128/2 H |
| 4,290,114 | 9/1981 | Sinay | 364/900 |
| 4,494,554 | 1/1985 | Van Dyke et al. | 128/734 |
| 4,494,869 | 1/1985 | Neumann | 356/36 |
| 4,532,937 | 8/1985 | Miller | 128/759 |
| 4,558,707 | 12/1985 | Miyamae et al. | 128/683 |
| 4,588,943 | 5/1986 | Hirth | 324/61 P |
| 4,670,010 | 6/1987 | Dragone | 604/289 |
| 4,711,244 | 12/1987 | Kuzara | 128/632 |
| 4,723,554 | 2/1988 | Oman et al. | 128/664 |
| 4,727,310 | 2/1988 | Hashimoto et al. | 324/157 |
| 4,796,182 | 1/1989 | Duboff | 364/413.29 |
| 4,860,753 | 8/1989 | Amerena | 128/632 |
| 4,864,226 | 9/1989 | Tachimoto et al. | 324/157 |
| 4,911,544 | 3/1990 | Walsh | 350/600 |
| 4,966,158 | 10/1990 | Honma et al. | 128/734 |
| 4,984,177 | 1/1991 | Rondel et al. | |
| 5,001,436 | 3/1991 | Scot et al. | 324/689 |
| 5,077,476 | 12/1991 | Rosenthal | 128/633 |
| 5,097,830 | 3/1992 | Eikefjord et al. | 128/419 D |

FOREIGN PATENT DOCUMENTS

| | | |
|---|---|---|
| 2671477 | 7/1992 | France . |
| 3125494 | 1/1983 | Germany . |
| 8701560 | 10/1987 | Germany . |
| 4039214 | 8/1991 | Germany . |

Primary Examiner—Max Hindenburg
Assistant Examiner—Eric F. Winakur
Attorney, Agent, or Firm—Fulwider Patton Lee & Utecht, LLP

[57] ABSTRACT

A skin condition analyzer with selectable modes of operation includes a probe apparatus for generating a skin condition signal representative of the moisture content of the skin and a processor that adjusts the skin condition signal in accordance with environmental components, such as temperature and humidity, to arrive at an overall skin condition signal. The skin condition is displayed visually and communicated audibly through a voice synthesizer system, having selectable languages. The modes of operation include single point random measuring and multiple point patterned measuring for compiling a composite skin analysis report.

25 Claims, 15 Drawing Sheets

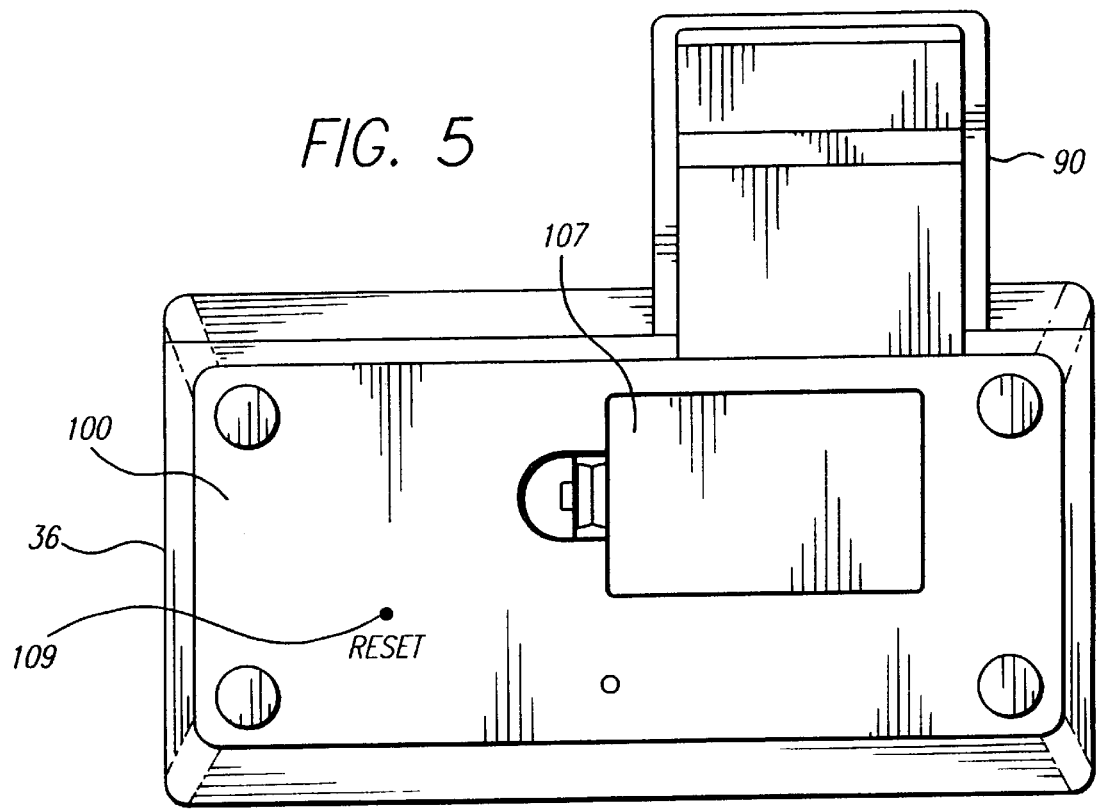
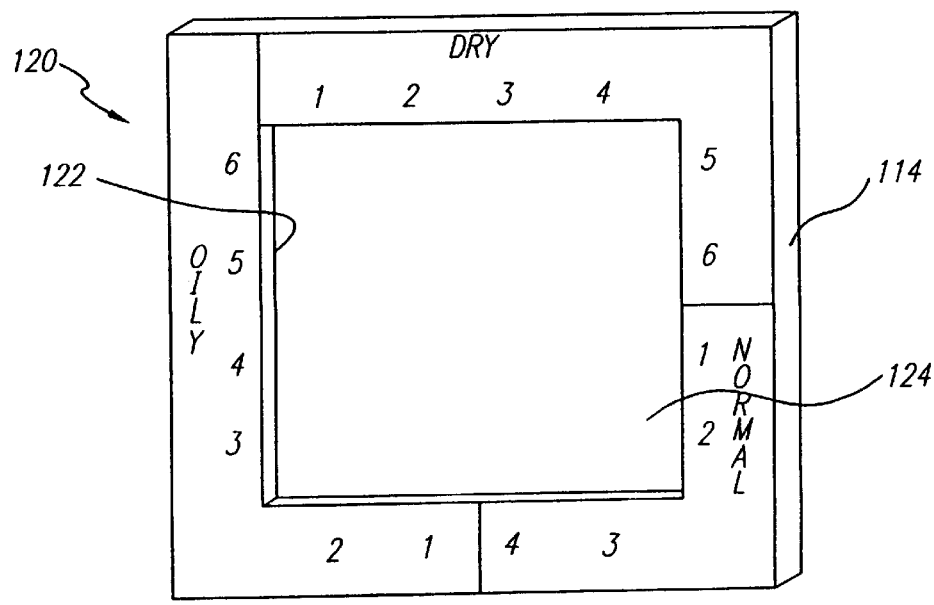

SKIN ANALYZER WITH SPEECH CAPABILITY

This is a continuation of application Ser. No. 08/615,395 filed Mar. 12, 1996, now abandoned.

BACKGROUND

The invention relates generally to skin analyzers and more particularly to skin condition analyzers with audible and visual outputs.

Measurements of a person's skin condition can be useful in various fields, one of which is the application of cosmetics to the skin. Numerous types of cosmetics are available; however, their successful use in many cases depends on the person's skin type or condition. To aid the consumer in this regard, the cosmetics industry has adopted several standardized indices characterizing skin condition. One such index classifies skin condition into four categories: "dry", "dry/normal", "normal/oily" and "oily". Another index classifies skin condition into three basic categories: "dry", "normal", and "oily", and if the measured skin condition crosses two categories, an additional category labeled "combination." Consistent with these indices, some cosmetics manufacturers place labels on their products that indicate the particular index being used and the category each product is designed for. Thus, a proper determination of the skin condition of the person can be important in obtaining the appropriate cosmetics product.

To make an accurate determination of a person's skin condition, a variety of factors should be considered including the general condition of the skin, its degree of moisture balance, the texture of the skin, the skin's elasticity, pore visibility, and facial creases. These factors should be taken into account at several locations on the face including the forehead, eyes, nose, cheeks, mouth, chin, jaw, ears, throat and hairline. Additionally, skin tone has been found to affect the determination of skin condition. The production of sebum and melanin, which affect the moisture content of the skin, appears to be affected by the skin tone.

In addition to the physiological factors noted above, it has been found that environmental factors may also affect skin condition and should be considered in making a skin condition determination. Environmental factors commonly define what is known as the human "comfort level" and may alter the skin condition during the time that it is undergoing condition analysis. For example, the air temperature and relative humidity may significantly alter the moisture content of a subject's skin and should be taken into account when making measurements. These effects are discussed below in more detail.

Skin condition also varies depending upon the particular location of the face being considered. It has been found that the glands that secrete the most oil onto the face are concentrated in the center of the face, most often around the nose, forehead and chin. These specific areas together commonly comprise what is referred to as a person's T-zone. The skin condition at these locations may differ substantially from the skin condition at other locations of the face. If one were to select a cosmetic product based on this area of the face alone, that product may not be as suitable for other areas of the face. Thus, it would be desirable to consider other locations of the skin in the determination of the proper cosmetics for application to the subject.

Devices that assist cosmetologists and others in measuring the moisture content of a subject's skin for the purpose of selecting the proper cosmetics for that subject have been available. While prior devices have been introduced that can measure moisture content, they often measure the skin condition at only one point on the face at a time as a "random" measurement. Thus, to get a composite analysis of the face, for example a person's T-zone, multiple measurements of the face must be made, with the separate results averaged manually by the operator of the device to obtain an overall skin condition. Manual calculations are undesirable because of the time required and inconvenience caused in performing them and the increased possibility of error. On the other hand, it is sometimes desirable to be able to make a single measurement at a single location of the face.

Thus, it would be desirable to provide an analyzer that has the capability of both providing a skin condition result based on only a single measurement and of providing a skin condition result based on multiple measurements as desired. In the case of multiple measurements, it would also be desirable for the analyzer to automatically perform any necessary calculations and automatically indicate the complete result so that manual calculations are obviated.

Furthermore, it is desirable that skin condition analyzers have a high degree of versatility. As mentioned above, different manufacturers use different indices for skin condition with different categories within the indices. A skin condition analyzer that is capable of providing an output for only a single index may be unusable for the products of other manufacturers who use different indices. Purchasing multiple skin condition analyzers is one option, however costs may increase if different configurations are necessary. A single analyzer that has the capability of providing an analysis result for different indices through minor physical modifications and minor programming changes would provide an improvement in the art while maintaining lower costs.

Another drawback with prior skin condition measurement devices is the failure of those devices to consider the subject's comfort level in determining the skin condition. In particular, temperature and humidity may have a substantial impact and should be considered. In a department store, where the majority of such analyses take place, an air conditioning system, or lack thereof, may substantially affect the subject's comfort level. For example, the comfort level may cause the skin to become temporarily dry or at the other extreme, moist with perspiration. This occurrence can cause a resulting skin condition determination to be artificially high or low, giving an inaccurate reading of the true skin condition under normal environmental conditions. It would be desirable to consider the subject's comfort level in making a skin condition analysis so that artificial effects may be recognized and accounted for.

In addition to the problems discussed above, prior skin measurement devices, also have failed to provide a convenient communication interface for the operator. Conventional skin analyzers often include only a visual display to communicate the resulting skin condition measurement. This places a burden on the analyzer operator to not only visually monitor where the skin probe or probes are being placed on the subject, but to also visually monitor the result displayed by the analyzer. Visually monitoring the analyzer's display can be difficult in low light conditions depending on the type of display used and can also be difficult in high light conditions due to glare on the display. In addition, some prior analyzers do not indicate when a measurement is complete and the operator has to guess when the probe or probes have been applied to the subject long enough to complete the measurement. Removing the probe too soon will result in an incomplete measurement and possibly an inaccurate reading.

Thus, the need exists for a skin analyzer to provide audible indications to the operator of the progress of the measurements. In particular, the need exists to inform the operator that the sensing procedure at this particular skin location is complete and that the entire measurement process of this subject's skin condition is complete. Additionally, it would also be desirable for the analyzer to automatically make a recommendation of the proper type of cosmetic product to match the measured skin condition.

Skin analyzers may be subject to abuse in department stores and in other environments. For example, they may be dropped, the probes may inadvertently be shorted together, and liquids may be spilled on them. Additionally, it is highly desirable that such analyzers be made available at a relatively low cost so that their benefits be made available to as many people as possible. It is therefore desirable that in addition to being accurate, that such analyzers be robust and able to withstand abuse as well as have a relatively low cost.

Due to the existence of different languages between countries of the world and in many cases, the multi-lingualism within each country, it would also be desirable to have an analyzer that can provide its output in different languages. Providing a skin analyzer that can communicate its measurement in different languages while maintaining relatively low manufacturing costs can pose difficulties.

Hence, those skilled in the art have recognized a need for a skin condition analyzer having the capability of providing multiple sensing modes while compensating the measurements for environmental conditions. The need also exists for such a device having the capability of providing an audible output for communicating the status of the measurement process and the skin condition measurement result and recommending cosmetics products to operators who speak different languages while at the same time lowering manufacturing costs. There is also a need for an analyzer that is versatile enough to be easily configured to provide its analysis in more than one manufacturer's index. The invention fulfills these needs and others.

SUMMARY OF THE INVENTION

Briefly and in general terms, the present invention is directed to measuring the condition of skin. Multiple sensing probes are used for contact with the subject's skin and provide an output probe signal to a processor. The processor compares the output probe signal to a plurality of stored threshold levels, and provides a skin condition signal representative of the comparison. A display device receives the skin condition signal and provides a visual display representative of the skin condition signal.

In an aspect of the invention, a replaceable lens is mounted adjacent the display to provide a reference scale indicating predetermined classifications of skin. In accordance with the reference scales, the analyzer operator can more easily select the appropriate cosmetics for the subject based on the measurement. In another aspect, an audible output device provides the skin condition measurement determined by the analyzer in a selected language. In a more detailed aspect, an audio generator provides an audible cue concerning certain actions undertaken by the analyzer. In one case, the audio generator provides a tone to indicate that the measurement is complete. In another case, the audio generator provides a tone to indicate that the analyzer has terminated power to itself due to inactivity.

In other aspects of the invention, the analyzer considers environmental components or factors in determining the skin condition measured. In one case, the ambient temperature is measured and the analyzer operator may adjust the analyzer according to that temperature. In another case, the relative humidity is measured and an adjustment may be made depending on the level measured. In yet a more detailed aspect, the relative humidity and temperature are determined and if the processor determines them to be a factor, the analyzer operator is cued to select the humidity adjustment mode of the analyzer. In the humidity adjustment mode, the analyzer will adjust the skin condition measurement according to the level of humidity sensed.

In a further aspect of the invention, the analyzer can be placed in one or more multiple measurement modes in each of which a plurality of measurements must be taken of the subject before the analyzer will determine a final skin condition. In a detailed aspect, the analyzer informs the analyzer operator audibly of the completion of each measurement of the program of multiple measurements so that the operator knows to move to a different location of the skin for the subsequent measurement. After the last measurement of the programmed plurality of measurements has been completed, the analyzer will then process all of the measurements to determine the final skin condition. In one particular aspect, the processor will average the multiple measurements to make the final skin condition determination.

Other features and advantages of the present invention will become apparent from the following detailed description of embodiments and the accompanying exemplary drawings.

BRIEF DESCRIPTION OF THE DRAWINGS

FIG. 2b presents a shape of a pointer icon used as a skin condition indicator icon on a display in one embodiment;

FIG. 5 is a bottom view of the skin analyzer of FIGS. 2, 3, and 4 showing a battery compartment cover and a reset switch;

FIG. 6 is an enlarged perspective view of an alternative lens cover similar to the cover shown in FIG. 2 but incorporating an alternative skin condition index or reference scale;

DETAILED DESCRIPTION OF THE PREFERRED EMBODIMENTS

Figure 1:
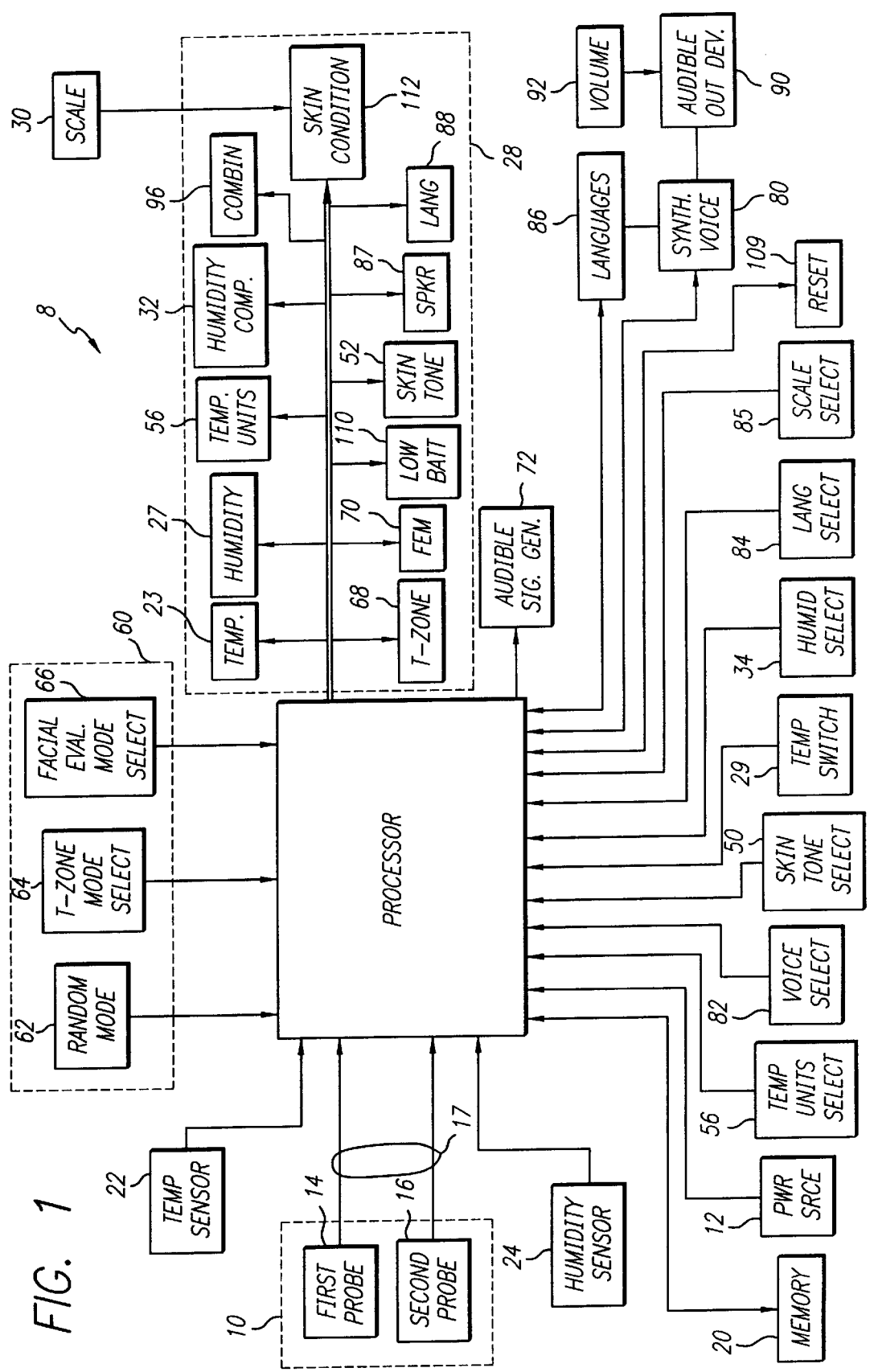
FIG. 1 is a block diagram of a skin analyzer incorporating features of the present invention.

Referring now to the figures in which like numerals represent like or corresponding elements among the several views, in FIG. 1 there is shown a skin condition analyzer 8 having a probe apparatus 10 for contacting a person's skin with probes and generating a probe output signal proportional to the sensed skin. In this case, the probe apparatus comprises two separate probes 14 and 16 that are configured to be placed at separated positions on the skin of the subject's body. The probes have a voltage between them that is applied to the skin of the subject by contact of the probes thereby causing a current to be generated, the level of which depends on the skin condition. This current is carried as a probe output signal 17 to a signal processor 18 that processes the probe output signal 17 to make a skin condition determination.

A power source 12 provides operating power to the processor 18 and the probes as well as other components discussed below. In one case, the power source comprises a battery and in another case, the power source may comprise wall power through the use of an AC-to-DC converter (not shown).

The processor 18 is programmable and may include input filtering circuitry and signal amplification components to improve signal quality for subsequent processing as is well known in the art. Memory 20 is accessible by the processor for carrying out arithmetic computations and preprogrammed instructions for processing the probe output signal into a resultant skin condition signal. The memory 20 may include ROM, RAM, and/or other types of memory devices and is shown here as a single box only for clarity of illustration.

In addition to the probe apparatus 10, the system 8 shown also includes an environmental sensor, in this case, two environmental sensors. This embodiment includes a temperature sensor 22 that senses the ambient temperature to which the skin analyzer and the subject are exposed and an humidity sensor 24. Referring now to both FIGS. 2 and 3, the processor receives the temperature sensor signal, processes it into a Fahrenheit or Centigrade format, or both, and provides it to a display 28 for a temperature display 23 of the temperature measured for viewing by the analyzer operator. The operator may operate a temperature switch 29 having an associated temperature scale 31, shown in FIG. 2a, to place the pointer 33 of the switch opposite the closest temperature value on the scale corresponding to the temperature displayed 23 by the processor 18. The position of the temperature switch 29 is sensed by the processor 18 and used in its calculations of the skin condition of the subject.

In the embodiment shown in FIG. 1, the humidity sensor 24 is also connected with the processor 18 to detect the ambient environmental humidity of the analyzer and the subject whose skin condition is being tested. The humidity sensor signal is used as an environmental compensation factor by the processor 18, as was the signal from the temperature switch 29 in determining the skin condition of the subject. The amount of such compensation for relative humidity depends upon the processor 18 instructions programmed into the memory 20.

In the embodiment shown, the processor 18 receives an humidity signal from the humidity sensor 24 and displays 27 (FIG. 2a) a percentage indicative of the relative humidity corresponding to the humidity sensed. Relative humidity values above 66% with a temperature above 27° C. (80° F.) will cause the processor 18 to command the display 28 to flash the temperature display 23 and the humidity display 27 to prompt the operator to press the humidity switch 34 (FIG. 3) to switch on the humidity compensation mode. Referring also to FIG. 3, the humidity switch 34 for activating the humidity compensation mode is shown on the back panel of the housing 36 of the analyzer and is labeled here as "Moisture". Depressing the humidity switch 34 causes a predetermined humidity compensation factor to be applied to the skin condition measurement by the processor 18 during processing. However, for relative humidity values less than 66% with a temperature of less than 27° C. (80° F.), no such prompt 32 will be displayed and even if the Moisture switch 34 is activated, the processor 18 will not apply the humidity compensation factor at that time. Rather, the displayed relative humidity reading 27 will be for information only. However, if the Moisture switch is activated when the sensed relative humidity is below the predetermined level, the processor will automatically apply the humidity compensation factor should the sensed humidity increase to the predetermined level; i.e., 66% in this embodiment, and the temperature increase to 27° C. (80° F.). Other arrangements for humidity compensation are possible, for example, the relative humidity threshold may be other than 66%, the threshold temperature may be other than 27° C. (80° F.). Temperature may be given less, or more, significance in determining the comfort level of the subject.

In another embodiment, the signals from the temperature sensor 22 and/or the humidity sensor 24 may be directly accessed by the processor 18 from the sensors and used in determining the skin condition of the subject rather than having to refer to a manually set temperature switch 29 position or wait for activation of the Moisture switch 34. In such an automated embodiment, the processor 18 automatically adjusts the skin condition measurement according to the received temperature sensor signal and humidity sensor signal.

A skin tone select switch 50 (FIG. 3) labeled here as "Ethnic" is meant to be activated by the analyzer operator when the subject has skin of a certain darkness. Activation of the switch 50 causes the processor 18 to adjust the resulting skin condition signal based upon a predetermined level corresponding to the relative physiological differences known to exist between skin types of substantially different tone. When this switch 50 is activated, the processor 18 also commands the display 28 to display a skin tone icon 52 to alert the operator that this compensation program is operating.

Operation of the skin analyzer 8 will also depend upon the desired mode of use 60 (FIG. 1) as selected by the operator. In accordance with the present embodiment, three modes of use are offered. These are referred to as the random mode 62, the T-zone mode 64, and the facial evaluation mode ("FEM") 66. The random mode 62 is the default mode and allows the operator to make a point measurement of the skin with a corresponding individual readout of the skin condition at that point. The T-zone mode 64 provides for a composite measurement of the subject's skin condition and requires six separate measurements in evaluating the skin condition. In the disclosed embodiment, this mode is labeled to indicate an evaluation patterned across the "T-zone" of a person's face (the forehead (two readings), nose (two readings), mouth and chin).

The facial evaluation mode 66 is also a composite measurement mode and comprises eight separate measurements used to determine overall skin condition. In both the T-zone mode and the facial evaluation mode, the processor is programmed to perform a plurality of skin measurements before a skin condition result is determined by the processor 18. Although these two modes are labeled in accordance with certain established skin patterns, one may take the respective plurality of measurement points on a subject's skin at other locations to obtain a composite skin condition analysis. The label T-zone and FEM are for operator convenience only. This feature increases the versatility of the analyzer.

Figure 2A:
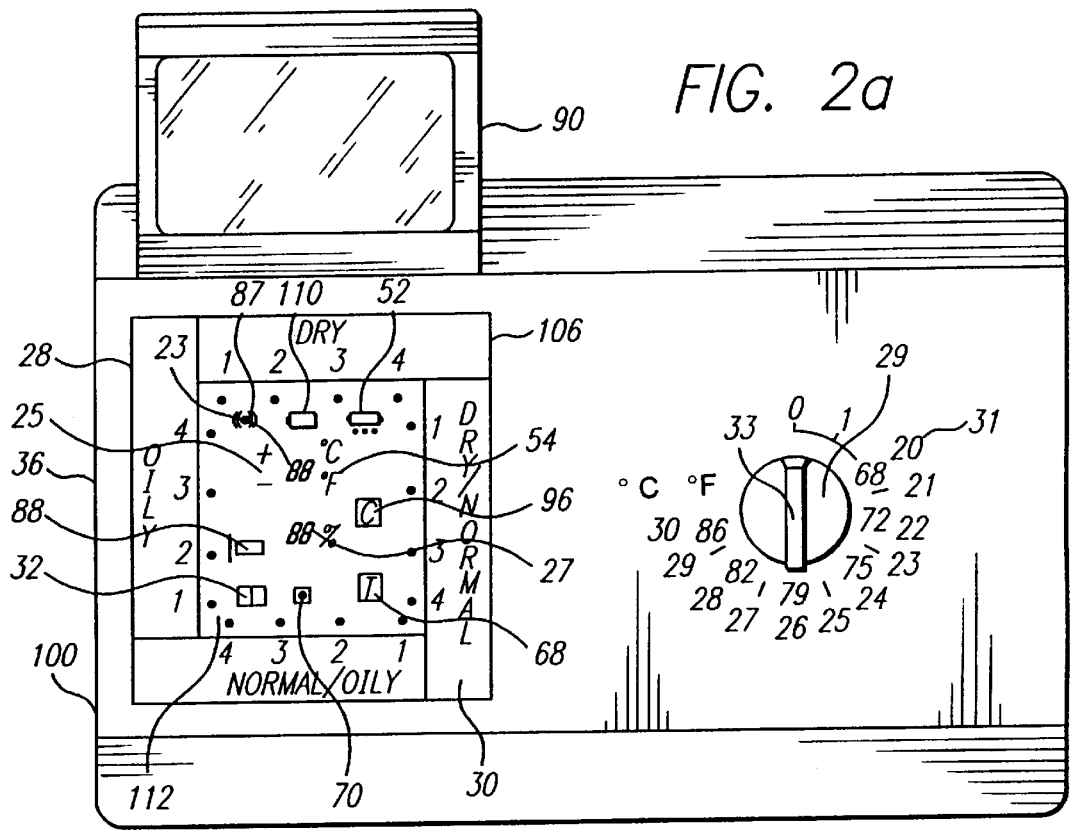
FIG. 2a is a top plan view of an embodiment of a skin analyzer showing a housing in which are mounted a display (with all of the display icons shown for clarity), a variable-volume speaker, and a temperature switch.
Figure 3:
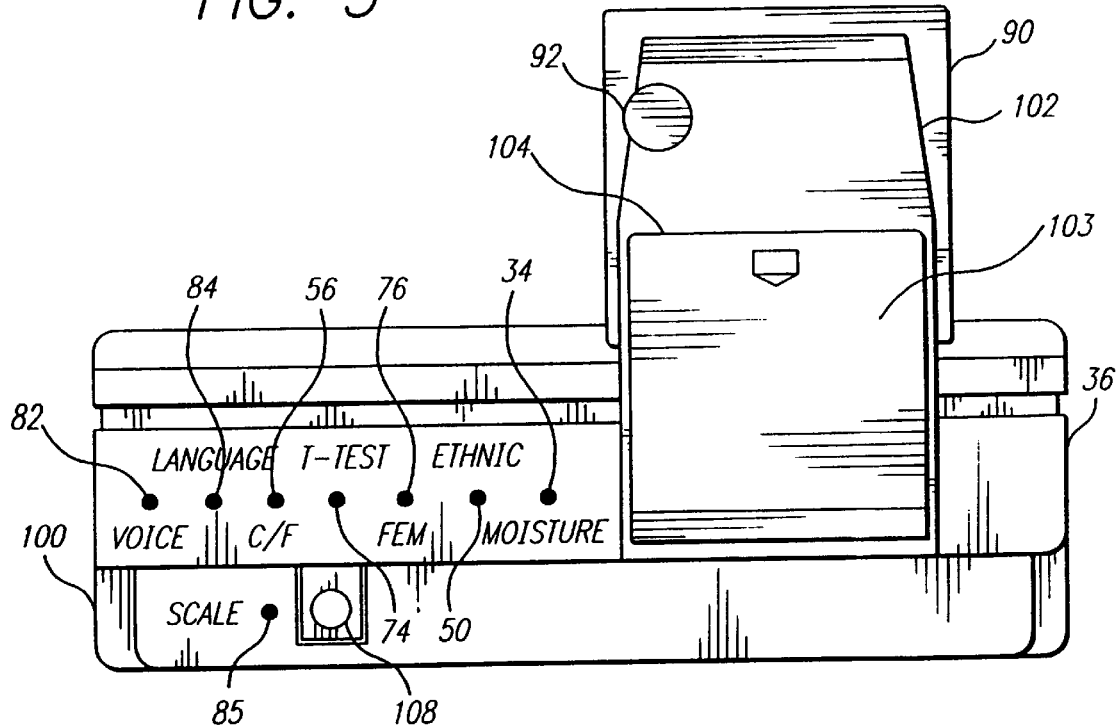
FIG. 3 is a rear view of the skin analyzer of FIG. 2 showing various switches and the speaker volume control.

The mode selected by the operator is displayed on the front panel as evaluation mode icons for the T-zone mode 68 and the facial evaluation mode 70 (FIG. 2a). If neither of these icons is illuminated, the analyzer is in the random mode 62.

In each of the T-zone and facial evaluation modes, the probes are placed on the subject's skin for measurement. The processor looks for measurement data and following a predetermined timed duration at that skin location, the processor determines a skin condition result for that particular location with an accompanying audible "beep" from an audible signal generator 72 (FIG. 1) prompting the operator to move the probe to the next skin location to proceed with the next measurement. Each of the individual skin location measurement results is stored in the memory 20 for later use. After the final measurement of the series, depending on the mode selected, the previous measurements are retrieved from memory and are processed together to produce a composite overall skin condition. In the present embodiment, the measurements are averaged in both the T-zone and the facial evaluation modes, except under certain conditions as will be described below.

A T-zone mode switch 74 and an FEM switch 76 for activating the respective modes are located on the back panel of the analyzer and are shown in FIG. 3. The last switch pressed has priority and turns the other modes off. Thus, activating the FEM switch 76 turns on the facial evaluation mode 66 and turns off the Random mode but then later activating the T-zone switch 74 will result in the T-zone mode 64 being on with the Facial Evaluation mode and the Random mode being off.

In the disclosed embodiment, each of the above switches cause a latching switch-type operation. That is, pressing the T-Test switch 74, FEM switch 76, Ethnic switch 50, and Moisture switch 34 all cause their respective effect to remain applicable until the respective switch is pressed again (or until a higher priority switch is pressed). As an example of their operation, if the FEM switch 76 were pressed engaging the facial evaluation mode 66 and the operator desires to return to the random mode 62, she would press the FEM switch 76 again. The latter action would disengage the FEM mode 66 and because the default mode is the random mode 62, the processor 18 would return to that mode. The above action may be modified by the mode priority system described above where the processor 18 gives priority to the last mode switch pressed to engage the mode and automatically disengages all other modes.

The above latching operation, mode system, and compensating factors provide an extremely versatile analyzer that has increased accuracy due to the consideration of environmental factors as well as because of the provision of composite analysis of the skin condition.

The operator also has the option of engaging a speech synthesizer 80 of the skin analyzer 8 by activating the voice select switch 82 (FIG. 3). Depending on which language the operator desires, the Language switch 84 may be activated to switch between the alternate languages stored 86 in the analyzer. For example, the stored languages may be English and Spanish. Pressing the language select switch 84 switches between the two. A speaker icon 87 on the display 28 indicates engagement of the voice or speech system and a language icon 88 on the display 28 indicates that the alternate language, typically a foreign language, has been selected. If the language icon 88 is not present on the display 28, the default language is active.

As will be noted, the ability to switch audio on or off 82 provides increased versatility to the skin condition analyzer in that the operator may in some cases desire an audio output but in other cases, desire only a visual indication of the analysis process. The analyzer in accordance with this embodiment provides this capability.

The speech synthesizer 80 acts as a parallel output with the display device 28. An audible output device such as a speaker 90 is provided for transducing the electrical signals into acoustic signals. A volume control 92 controls the output level of the speaker. Each language of the speech synthesizer 80 is contained in a separate memory device in one embodiment. Each language may contain particular words, phrases, or sentences in that language that are selected to correspond to the possible skin conditions or events that may occur during a measurement process. During manufacture, the proper memory devices for the customer are selected. For example, if the customer were located in the southwestern portion of the United States, the language memories may comprise an English memory and a Spanish memory. If the destination is Canada, English and French language devices may be installed.

In one embodiment, the language devices comprise EEPROM chips pre-programmed with certain words and phrases. However, other types of devices may be used. The same memory used to store processor programs may be used to store the language words and phrases in one embodiment. The analyzer may comprise a pair of identical IC sockets or mounting devices into which selected language chips having identical configurations may be mounted during manufacture. Because the respective language chips and the mounting devices are the same, manufacturing costs are lowered. Interchangeability of the language devices during manufacture allows for easy replacement and installation of equivalent devices having language memories to allow audible communication of the resultant skin condition in more than one language. The devices are interchangeable because the processor is programmed to call for a predetermined message from the language device and that device provides the appropriate message in its particular language.

In addition to the audible output device 90, an audible signal generator 72 is provided in the skin analyzer 8 to prompt the operator with an audible signal concerning activation of the unit, the expiration of predetermined timed durations during measurement, as discussed above, and the termination of power to the analyzer. In the composite measurement modes, a prompt will also be provided indicating the end of each of the plurality of measurements. Timing may be accomplished through the use of a timing device (not shown) that may comprise an internal clock or other device well known in the art. In one embodiment, the audible signal generator emits one beep tone when the analyzer is turned on, when the analyzer is turned off, each time a function switch is pressed, and at the end of a single skin measurement period. The analyzer also informs the operator of the completion of the required multiple measurements in a multiple measurement mode with two beep tones. Three beep tones are emitted when the relative humidity and temperature reach the level where the humidity mode should be engaged. The humidity display 27 also flashes. The audible signal generator 72 may prompt the operator for other purposes as well and other tone combinations may be used.

Reviewing the display 28 now in more detail with reference to FIG. 2a, the display device 28 receives processor outputs and is capable of visually communicating the skin condition of the subject as well as the measurements of the temperature and humidity sensors, and the status of various functions of the analyzer to a viewer. As discussed above, the display 28 includes respective indicators showing the measured ambient temperature 23 and measured relative humidity 27, and the temperature units (Fahrenheit or Centigrade) 54 selected, which is controlled by the temperature units switch 56 on the back panel of the analyzer. Also displayed are icons concerning humidity compensation activation 52 and skin tone activation 32 as discussed above. The display also includes a foreign language activation status icon 88, a low battery power icon 110, a T-zone mode icon 68, a facial evaluation mode icon 70, a speaker activated mode icon 87, and sixteen skin condition indicator icons 112 in the shape of dots, or the shape shown in FIG. 2b, used in combination with the reference scales 30 to indicate skin condition. Should the alternate icon 94 be used, the icon would be oriented so the smaller rectangular side 95 would point to the numbers on the reference scales. All skin condition icons 112 are shown in FIG. 2a for illustration purposes only. Normally during actual operation, only one such icon would be on and the remaining fifteen would be off. A "combination" icon 96 is also provided for use with those classifications having scales that do not show a combination skin condition. The temperature range displayed by the temperature numbers 23 is confined to 20° C. to 30° C. (68° F. to 86° F.). Should the temperature exceed 30° C. (86° F.), the numbers 23 will indicate 30 but the plus (+) icon 25 will be activated to inform the operator that the temperature is actually above the indicated temperature. Similarly, if the actual temperature is below 20° C., the numbers will indicate 20 but the minus (−) icon 25 will be activated informing the operator that the actual temperature is less than that indicated. In one embodiment, the analyzer would operate above 30° C. but would use the 30° C. settings. Similarly the analyzer would operate at temperatures below 20° C. but would use the 20° C. settings.

Referring now in more detail to FIGS. 2a, 3, 4, and 5, the skin analyzer shown includes a generally rectangular housing 36 having a planar top surface and supported on its underside by a wedge-shaped base 100 to slightly elevate one longitudinal side of the housing. The elevated side is formed at one end with a support mount 102 to secure the speaker 90 and house a battery 104. A volume control knob 92 is mounted to the upper rear portion of the speaker mount 102 for adjusting the speaker loudness. A battery cover 103 is shown that covers two 1.5 VDC batteries (not shown). The planar surface of the housing is formed with an access window to allow viewing of a liquid crystal display "LCD" 28. The window is bordered by a slightly recessed rectangular groove 105 for receiving an interchangeable lens cover 106. Positioned proximate the window on the planar top is the temperature selection switch 29. A plurality of switches (discussed above) are mounted on the back of the housing and a probe apparatus 10 receiving jack 108 is available to receive the wiring of the probes.

Shown on the bottom panel of the analyzer in FIG. 5 is a battery cover 107 and a reset switch 109 used to reset the processor in the event of a malfunction and when changing batteries.

The temperature selection switch 29 comprises thirteen positions for selecting temperatures and controlling the analyzer to an "on" or "off" status. The first two positions of the switch control the on/off state of the device and are labeled "0" and "1". The remainder of the thirteen positions reflect an expected range of temperatures in Fahrenheit and Celsius, from which one will be selected. Selection of the proper temperature is made after the analyzer 8 is turned on and the temperature display 23 observed for the ambient temperature.

The interchangeable lens cover 106 comprises a skin characterizing index having reference scales 30 that form a border and cooperate with the skin condition icons 112 to indicate the measured skin condition of the subject. The reference scale 30 shown in FIG. 2a has four sides or categories labeled "DRY", "DRY/NORMAL", "NORMAL/OILY", and "OILY". Additionally, each side has a degree or severity indication in the category shown by the series of numbers ranging from one to four for a total of sixteen dots. After making the proper measurements of the subject, one skin condition icon 112 would be turned on adjacent one of these four sides and adjacent one of the severity numbers in the side. The reference scales 30 shown in FIG. 2a are an industry standard with many cosmetics rated according to these reference scales.

However, another industry standard index comprising a set of reference scales 114 is shown in FIG. 6. In FIG. 6, the reference scales 114 are divided into three classification categories, "DRY", "NORMAL", and "OILY" also with a range of numbers in each category indicating severity. In the case of the "DRY" and "OILY" categories, the severity numbers range from one to six. In the case of the "NORMAL" category, the numbers range only from one to four. Should a skin measurement indicate that the subject's skin condition does not fall into one of these categories, but instead is a combination of categories, the combination icon 96 would be activated on the display rather than one of the skin condition icons 112. Other reference scales may be constructed with different numbering schemes. The processor 18 need only be programmed to activate the appropriate icon corresponding to the particular reference scales in use at the time.

Referring now particularly to FIG. 6, the interchangeable lens cover 120 includes a thin rectangular border 122 that surrounds a transparent window 124 formed of clear plastic or glass. The lens cover cooperates with the display 28 to give the operator a clear display of the measured skin condition as well as the status of particular aspects of the analyzer.

Figure 4:
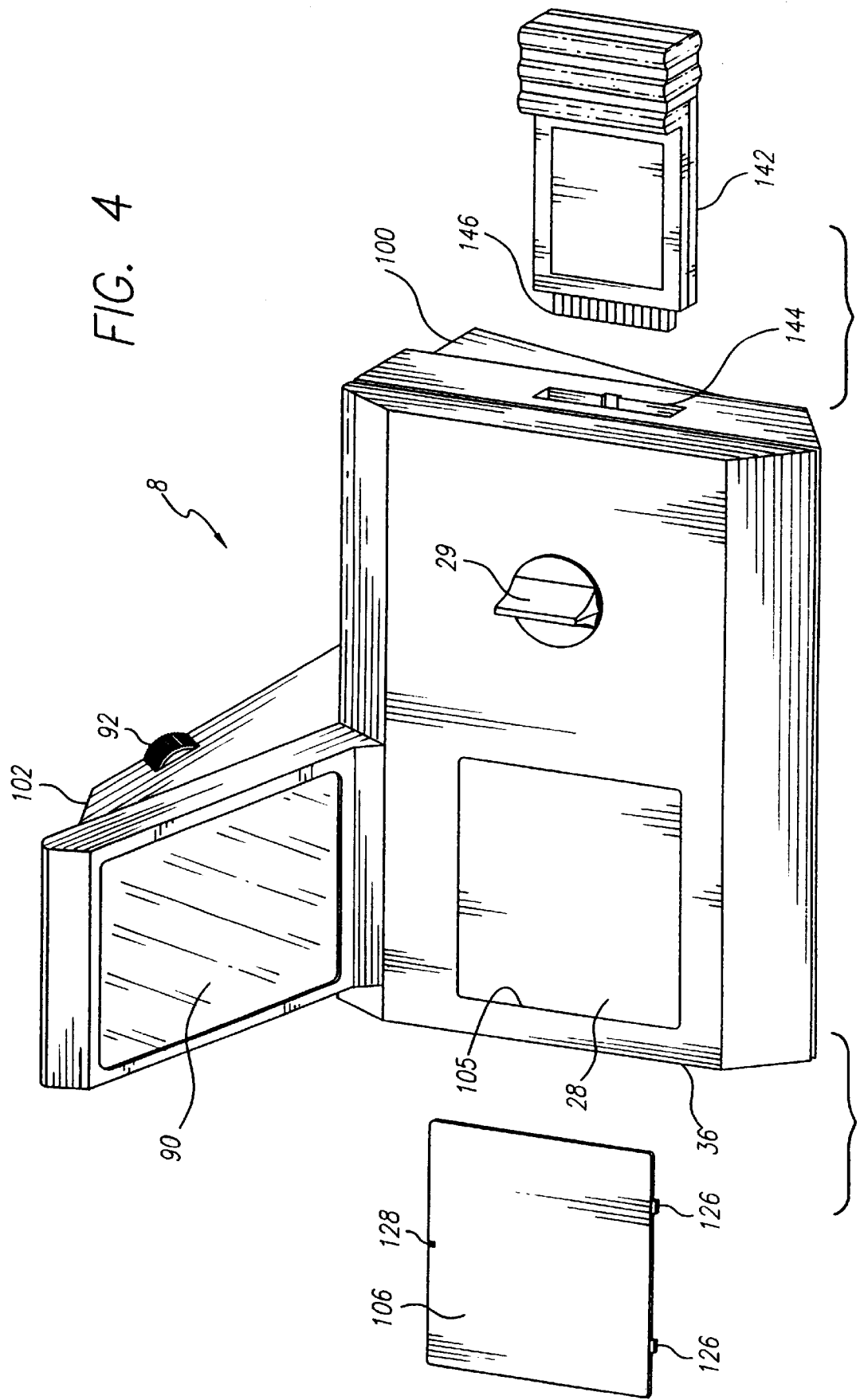
FIG. 4 is a perspective view of a skin analyzer incorporating features of the invention and demonstrating a replaceable lens cover and its attachment means as well as the mounting technique for interchangeable language modules.

More detail on a mounting arrangement for an interchangeable lens cover 106 is presented in FIG. 4. The lens cover comprises tabs 126 that are received in complementary slots (not shown) in the rectangular groove 105 over the display 28 face. As the tabs 107 are inserted in the slots, a hinge action is achieved and the upper surface containing a slot 128 is then rotated into position in the groove 105 in which the lens cover is held in position by a friction fit. Removal can be accomplished by inserting a tool in the lens cover slot 128 and prying the lens cover 106 out of the groove. Although the above-described mounting arrangement has been proven to be highly effective, other arrangements may be used. No reference scales have been shown on the lens cover 106 in FIG. 4 to retain clarity of illustration of the mounting arrangement.

Also shown in FIG. 4 is a mounting arrangement for a language device 142. In this embodiment, a first language device has been installed inside the analyzer at the factory and is not operator changeable. However, in FIG. 4 a second language device 142 can be installed by the operator by sliding it into a mounting slot 144 formed in the side of the analyzer body. The device includes electrical contacts 146 to mate with contacts in the analyzer for operation. During use of the analyzer, the second language device would be selected by activating the language switch 84 as described above.

In a further embodiment, the factory manufactured analyzer may have two language devices installed and the operator may install a third language device 142 by sliding it into the side slot 144. When the third language device is detected by the processor, the second factory-installed language device is overridden.

In an alternate embodiment, the slide mounted language device 142 may be the only language device mounted in the analyzer. To change languages, the operator would simply replace one sliding language device with another. While not as convenient as switching between two installed language devices, this embodiment would reduce the costs of analyzer manufacture in that only one language device is used.

As will be noted from the above description, a library of language devices may be collected by operators and installed as necessary. This also adds versatility to the analyzer described herein.

Referring again to FIG. 1, the processor 18 continuously monitors the battery 12 voltage level and if that level decreases below a threshold, the processor 18 controls a battery level warning icon 110 (FIGS. 1 and 2a) to appear on the display. Other battery characteristics may be monitored in determining the status of the battery instead of voltage or with voltage.

The display is then activated by the processor to display the skin condition determination it has made. At the same time, the skin condition determination is spoken by an audible output device such as a speaker 90, as is discussed in more detail below.

Figures 1, 7:
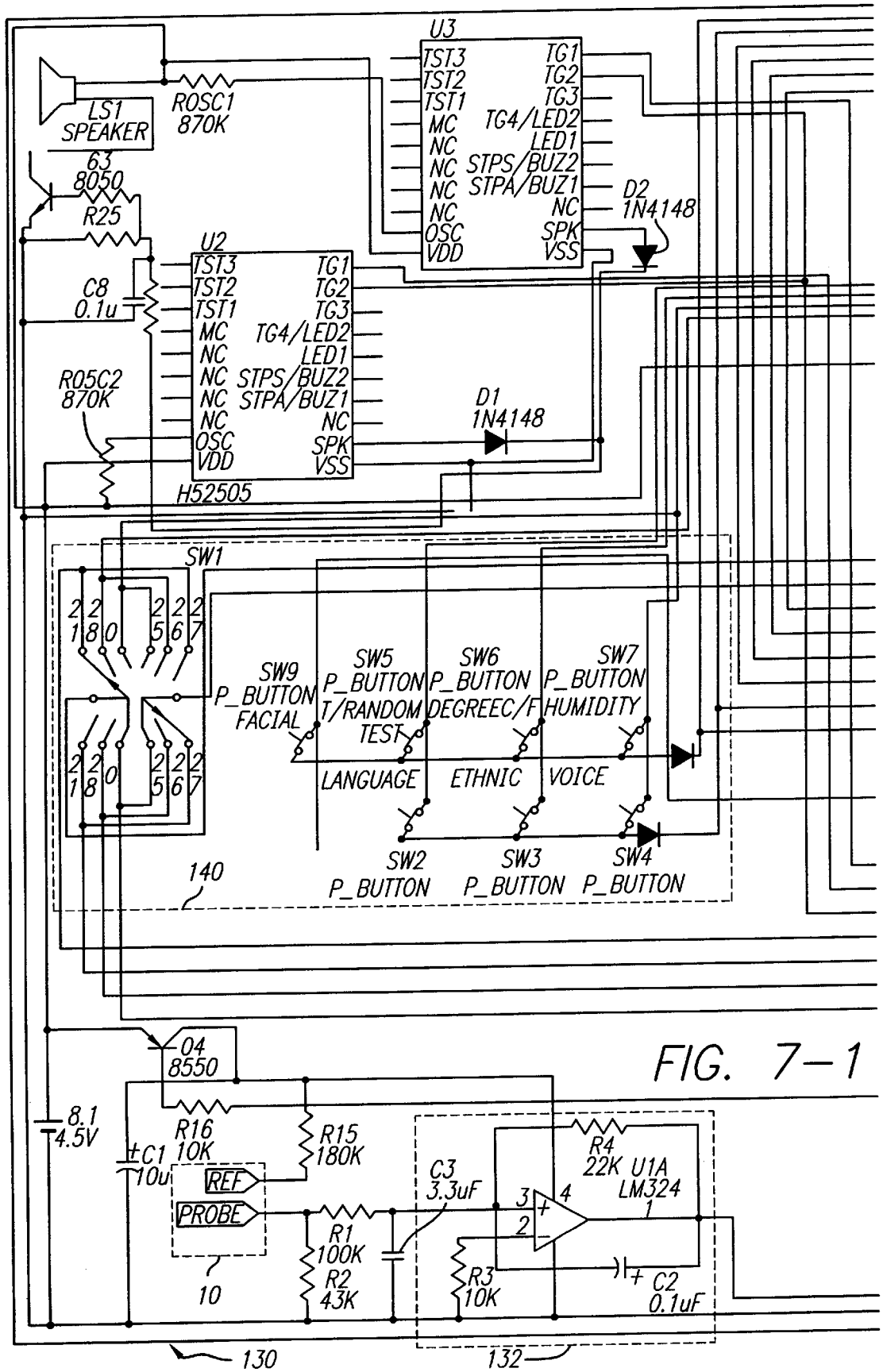
FIG. 7 is an electrical schematic of a circuit used in a preferred embodiment of the present invention.
Figures 2, 7:
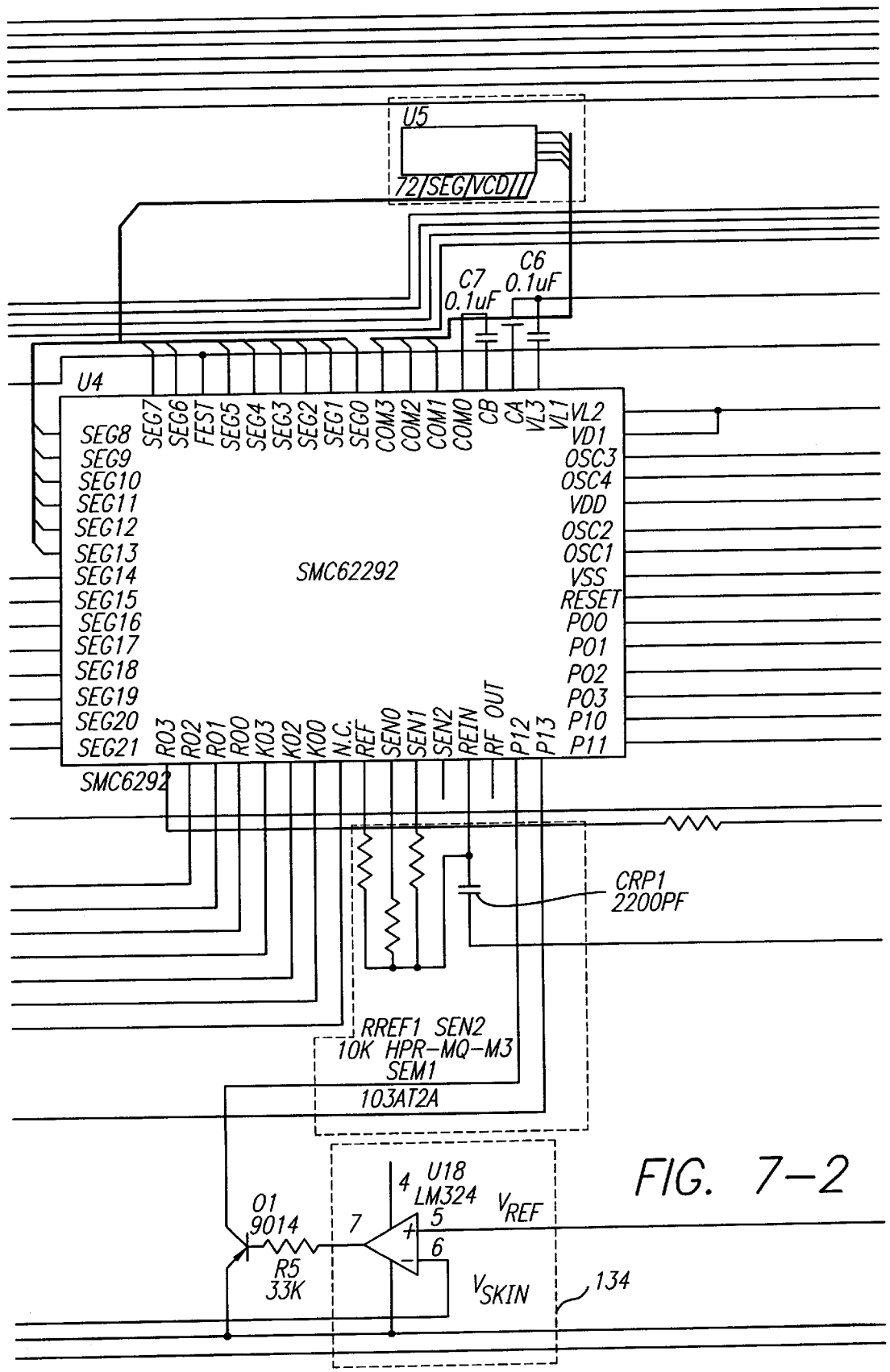
Figures 3, 7:
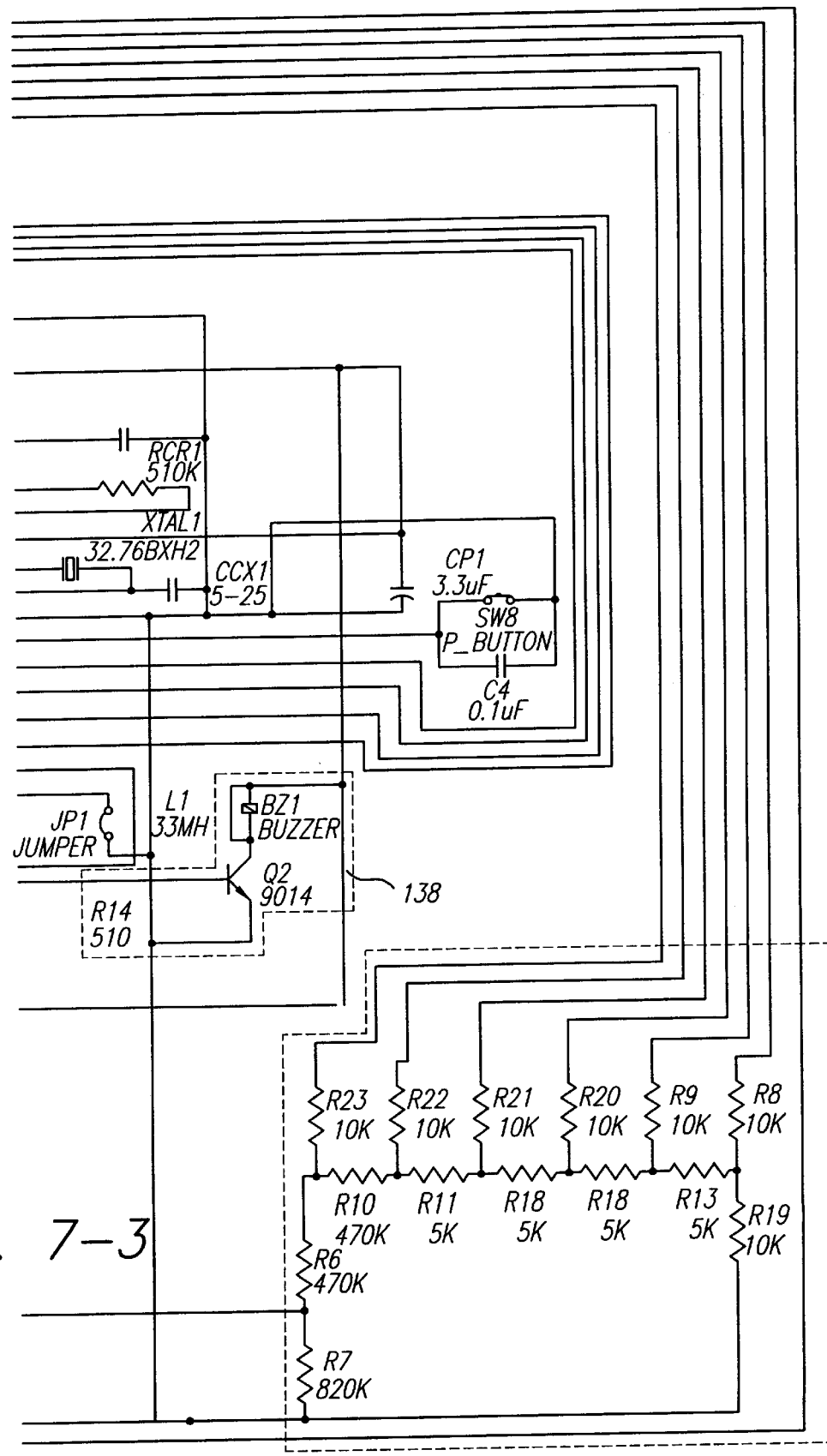

Referring to FIG. 7, a schematic diagram of an analyzer circuit 130 useful in determining the skin condition of a subject is presented. A microprocessor U4 has internal memory for storing threshold voltage levels, sensed voltage levels, and programming instructions. The analyzer circuit 130 includes a power source BT1. Preferably, conventional batteries staged to deliver 4.5 volts to the device electronics are used, with such voltage realized through the use of three 1.5 volt batteries or one nine volt battery with its output voltage divided as required. An AC-to-DC transformer (not shown) may alternatively be used to convert standard line voltage to the specified level for the analyzer.

The probe apparatus comprises a first probe REF and a second probe PROBE connected to the analyzer circuit through two twenty-four strand copper leads that plug into a mono jack 108 at the back of the housing 36 (FIG. 3). The plug is removable from the jack 108. The first probe REF serves as a skin reference and is connected at one end through a resistor R15 to the collector of a transistor Q4 while the other end is left floating. The emitter of transistor Q4 is tied to the power source anode to function as a current source for the first probe when the transistor Q4 is turned on. The second probe also has one end floating with the other end connected to resistors R1 and R2. Application of the probes to a conductive surface, such as a subject's skin, completes a circuit formed by various circuit elements BT1, Q4, R15, R1 and R2 and produces a voltage output at the resistor node defined by R1 and R2.

The output of the probe apparatus is filtered by a low-pass filter 132 that includes an input capacitor C3 and an internally compensated op-amp U1A configured with an RC feedback network defined by resistors R3, R4 and a capacitor C2. The output of the filter/amplifier is connected to the inverting terminal of a comparator 134. In addition to filtering unwanted frequencies, the op-amp U1A serves to boost the probe signal to a predetermined level for additional processing by the comparator 134.

The comparator 134 includes an op amp U1B with its output connected through the transistor Q1 to an input port P12 of the processor U4. Connected at the non-inverting terminal of the comparator 134 is the output of a voltage divider network defined by resistors R6 and R7. The source of the analog signal fed to the divider is a six-bit digital-to-analog converter defined by resistors R8–R13 and R18–R23. The digital-to-analog converter is configured as an R-2R network that is well known in the art and receives its six individual bit signals from the processor U4. The processor determines the probe output signal according to a binary search routine that uses the output of the transistor Q1 as feedback to the processor U4 to determine the voltage at the op amp 134 non-inverting terminal.

An LCD U5 is connected to the processor U4 terminals SEG0–SEG13 and COM0–COM3 and generates the display 28 in response to commands from the processor U4.

The analyzer circuit 130 also includes a voice synthesizer 136 having two programmable voice synthesizer control chips U2 and U3 to complement the visual display generated by the LCD control chip U5. The synthesizer chips are wired in parallel and utilize the ADPCM coding method to generate many types of desired voice effects. The inputs of the voice chips, TG1 and TG2, are connected to the processor output ports R00–R02. The outputs of the voice chips, SPK, are connected through blocking diodes D1 to drive a transistor Q3 that acts in combination with resistors R24, R25 and a potentiometer VR1 to produce a volume control for the speaker LS1. The resistors ROSC1 and ROSC2, connected to the voice chip oscillator outputs, determine the speed at which the synthesized message plays.

Changes in the visual skin condition display as the result of a lens cover change may be correspondingly modified by installing the jumper JP1 between processor pins P11 and VSS during manufacture of the analyzer. In another embodiment, an additional Scales switch 85 may be mounted on an external surface of the analyzer (see FIG. 3) that switches the analyzer between two or more indices. The operator would only then need to replace the lens cover with the appropriate cover. Upon sensing the activation of the switch, the processor would automatically accommodate its activation of skin condition icons 112 in accordance with the new scales installed and would automatically change the audio output as well.

Independent from the voice synthesizer 136 is an audio tone generator 138 comprising an audible buzzer BZ1 that generates an audible tone or beep upon the occurrence of certain conditions programmed into the processor U4. The buzzer is configured with a coil L1 connected across the buzzer terminals and driven by a transistor Q2 that receives on/off threshold signals from a processor output port R03.

Further referring to FIG. 7, the analyzer circuit 130 includes temperature and humidity sensors SEN1 and SEN2 respectively. The processor U4 includes special input ports SEN0 and SEN1 for connecting to the sensors that are tied together at a common node with a reference resistor RREF and a reference capacitor CRF1. The reference capacitor CRF1 in turn is connected through a pair of capacitors CP1 and CGX1 to an oscillator XTAL1 to introduce an oscillator signal across the respective sensors. Those skilled in the art will recognize the separate RC circuits configured by the parallel configuration of components RREF, SEN1 and SEN2 with CRF1 which generates respective RC output signals which the processor monitors and compares. Differences in the frequencies monitored between the reference RC circuit and the respective sensor RC circuits enables the processor to arrive at measurement values for the humidity and temperature sensors. This measurement technique is commonly referred to as R/F (resistance to frequency) conversion. The detected measurements are then conditioned for further processing by the LCD control chip U5 that generates a representative signal for display.

The operator controls 140 include the temperature selector switch SW1 and the button switches SW2 through SW7 and SW9. The button switches are the push-button type with biasing to the non-contact position.

Figure 8:
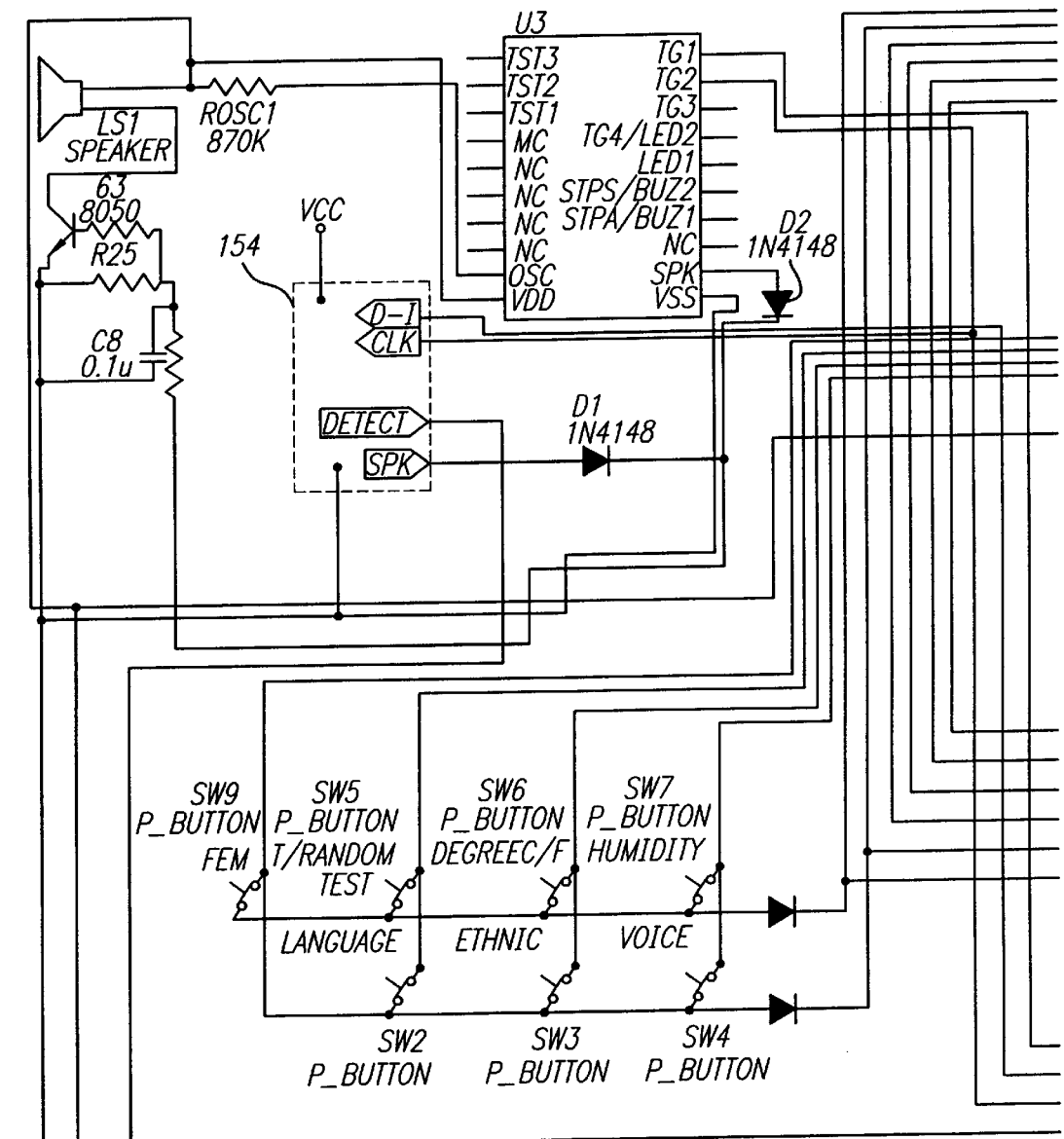
FIG. 8 is an electrical schematic of a circuit having automatic temperature and humidity compensation feature.
Figure 1:
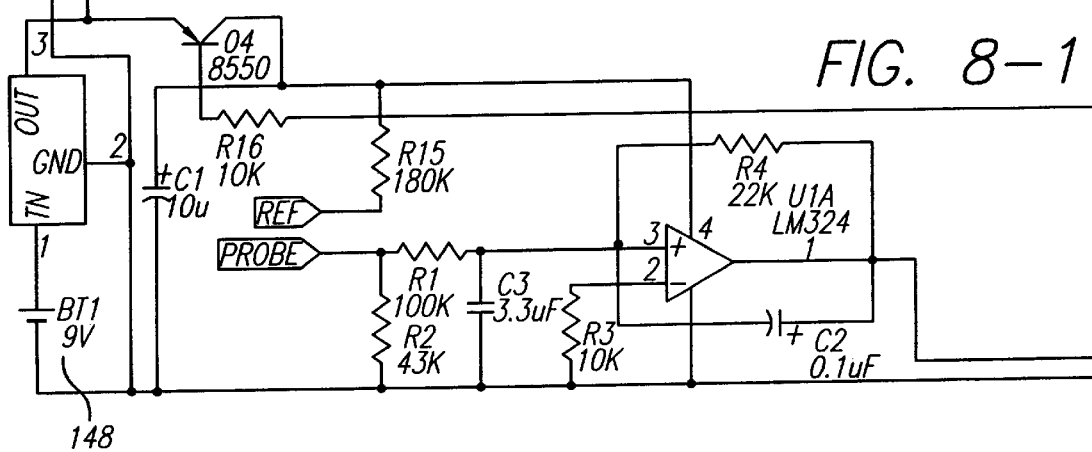
Figures 2, 8:
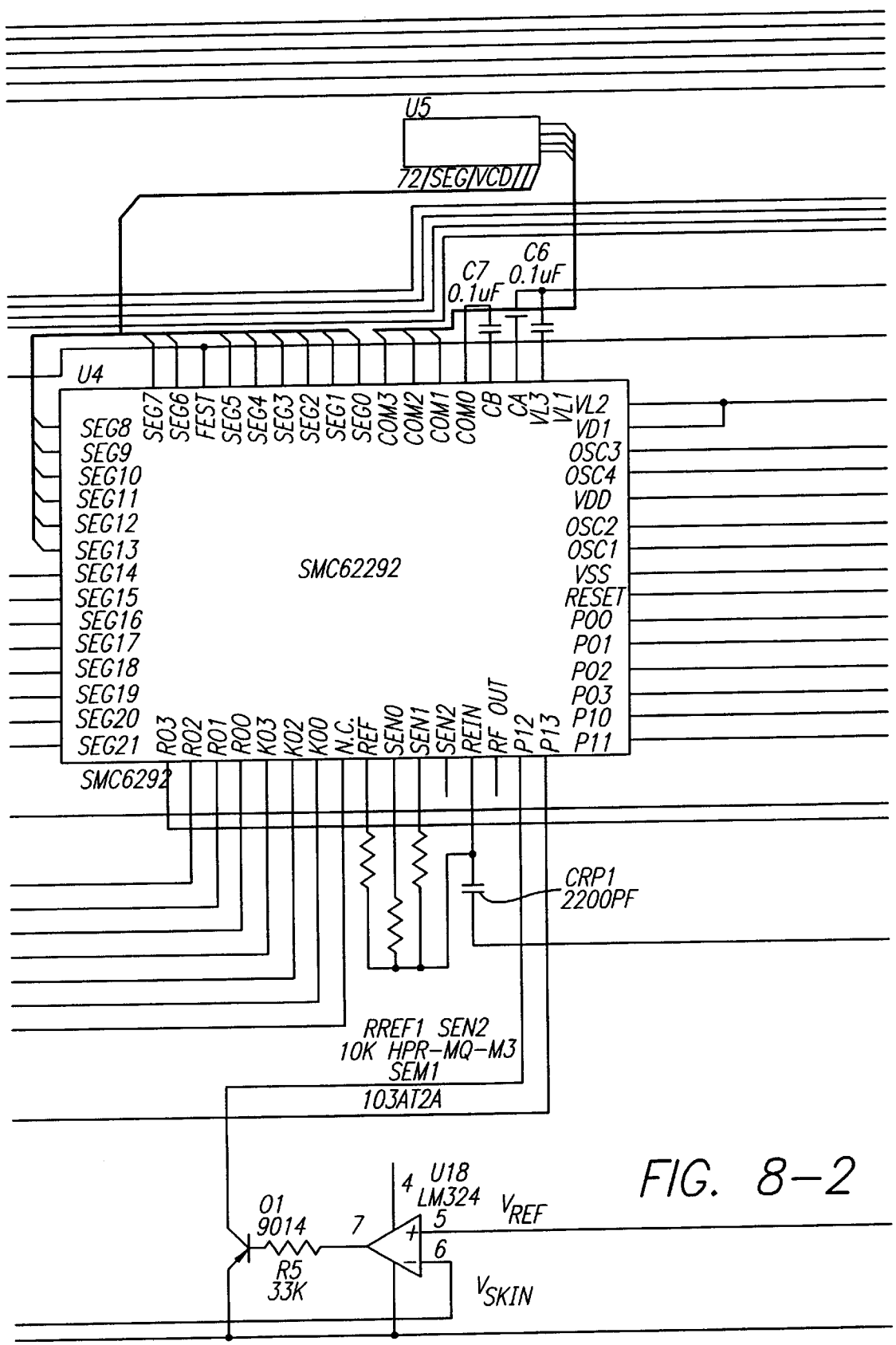
Figures 3, 8:
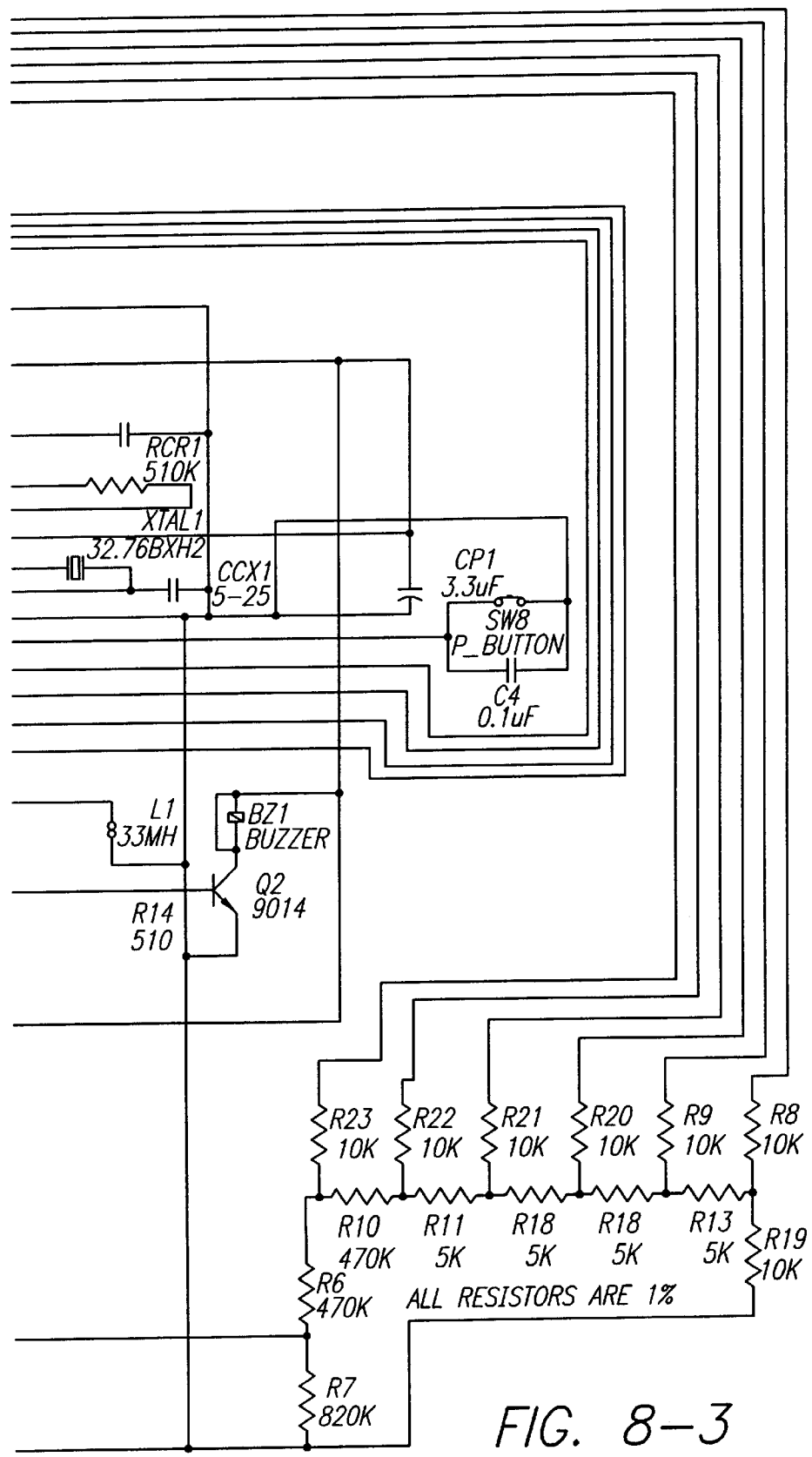

A listing of the component values or descriptions for the components shown in FIGS. 7 and 8 is as follows:

BT1 Battery
BZ1 Buzzer
CGX1 5–25 pF
CP1 3.3 μF
CRF1 2200 pF
C1 10 μF
C2 3.3 μf
C3–C7 0.1 μF
D1–D2 1N4148
L1 33 mH
LS1 Speaker
Q1–Q2 9014
Q3 8050
Q4 8550
RCR1 510K
ROSC1–2 1M
RREF1–10 10K
R1 100K
R2 43K
R4 22K
R5 33K
R6 470K
R7 820K
R10–13 5K
R14,17 510K
R15 180K
R16 5K
SEN1 103AT2B
SEN2 HS12P
SW2–8 Push Button
U1 LM324
U2–U3 W52532
U4 SMC6292
U5 72 Seg. LCD
XTAL1 32.768 kHz The probes may take many forms but in one embodiment, they comprised two separate probes for placement at separated positions on the subject's skin. In one example, the first probe REF would he held in the subject's hand while the second probe PROBE would be placed in contact with the appropriate part of the subject's facial skin. In one case, the face probe was constructed of T-304 high mirror polished stainless steel and took the form of a closed cylinder. The hand probe also was formed of T-304 high mirror polished stainless steel. Both had internal electrical contacts.

In the circuit shown in FIG. 7, the humidity sensor SEN2 comprised model HS12P or HS15P from Scimarec Company, Ltd., Chichibu Onada Building, 14-1 Nishi-Shimbashi 2-Chome, Nanato-ku, Tokyo Japan and the temperature sensor SEN1 comprised model AT103-2B from Ishizuka Electronics Corporation, 7-7 Kinishi 1-Chome, Sumida-ku, Tokyo, Japan. The voice synthesizer is available from Winbond Electronics Corporation, N. 2, R&D Road, Science Based Industrial Park, Hsinchu, Taiwan, R.O.C. The op amps U1A and U1B comprise LM324's made by many manufacturers. Devices U1A and U1B may be part of a quad comparator such as an LM324. The processor U4 was an SMC6292 micro-processor unit (MPU) available from Epson. The liquid crystal display used in the embodiment shown was an LCDM1227, one-fourth duty available from WINTEK Corporation, 9-2 Chien-Kuo Road, Tepz Tantzu, Taichung, 427, Taiwan ROC.

Returning now to the comparator 134, the level of the probe output signal as filtered and amplified is determined by the processor by comparison to the voltage developed at the R6/R7 node. The device U1B is used as a comparator. It compares the voltage between pins 5 and 6. The voltage at pin 5 is generated by the CPU (Vref). The voltage at pin 6 is generated from the probe (Vskin). The skin voltage Vskin will be filtered and the noise will be amplified to a measuring value. The CPU U4 will change the voltage at pin 5 to determine the voltage at pin 6. The CPU U4 gets the voltage value at pin 6 and then finds the skin condition level from a table stored inside the CPU U4. Furthermore, the CPU U4 will announce the level found by display on the LCD 28 and by voice function is activated.

After the probe output voltage is determined, the processor classifies that voltage into one of the four categories of the reference scales around the display by comparison to the temperature selected. The category, such as DRY, DRY/NORMAL, NORMAL/OILY, or OILY is selected as is the severity in the particular category. If the ethnic switch (skin type selection switch) has been activated, the number result is lowered by a predetermined value, such as three, and if the humidity compensation switch has been activated, the number result is also lowered by a predetermined value, such as four. However, if the result is less than one, the number is set to two.

Turning now to a description of the timing functions, in this embodiment, there are 2 Hz, 8 Hz, and 32 Hz timer interrupts inside the CPU U4. The 2 Hz interrupt is used to count the idle time. If there is no key input for ten minutes, the system will be automatically turned off. Moreover, the 32 Hz interrupt is also used to count the measurement time. If the test to the skin has been counted for five seconds, there is a beep tone to confirm the reading and stop the measurement.

Operation of the skin condition analyzer 8 begins by properly configuring the operator control interface. Typically, this includes first inserting the probe apparatus plug into the receiving jack. The operator then manually turns the rotary switch 80 (FIG. 2a) to the "1" position which turns the unit on. The processor 18 will immediately begin processing the sensed temperature and humidity of the surrounding area and generate steady state signals to the LCD 104 for displaying representative outputs indicative of such measurements. The operator then rotates the switch indicator to align the labeled temperature closest to the temperature displayed on the LCD. This enables the proper temperature compensation factor to be used for the processing of the probe output signal. If the measured relative humidity is 66% or greater and the temperature is 27° C. (800 ° F.), the operator will be prompted to activate the humidity compensation switch which will cause the processor to adjust the skin condition result according to a humidity compensation factor.

Instructions provided with the skin analyzer will advise that the skin tone switch 92 should be toggled "on" if the person's skin tone is of a predetermined tone. Activation of this switch causes the processor to apply an additional compensation factor to be taken into account in arriving at an accurate resultant skin condition signal.

Once the skin condition analyzer switches are configured for optimal performance, the operator is directed to use the probe apparatus 10 in a prescribed fashion to generate a probe output signal indicative of skin moisture content. The first probe 14 is taken into the person's hand while the second probe 16 is applied to a desired area of the face. The two probes contacting the skin operate as two nodes, with the skin between them acting as a variable resistor having a magnitude proportional to the moisture content of the skin.

Turning now to more details of the determination of the skin condition, both the T-zone mode and the facial evaluation mode will be described in the context of the skin condition index shown in FIG. 6 in which there are three categories of skin condition; DRY, NORMAL, and OILY. In the disclosed embodiment, sixteen measurement results are possible for each skin measurement; i.e., one of the sixteen icons 112 on the display 28 may be activated. These sixteen possibilities are divided up into the three categories, DRY, NORMAL, and OILY. As described above, in the T-zone mode, six individual skin measurements are taken before the final result is calculated and indicated. If five or more of those readings fall within one category, such as "DRY", the processor will report that category as the skin condition. However, if less than five readings fall within one category, then the category "COMBINATION" (icon 96, FIG. 2a) may be reported if any of the following conditions are met:

if 3 readings are $\leq 10$ and 3 readings >10
if 2 readings are $\leq 10$ and 4 readings >10
if 4 readings are $\leq 10$ and 2 readings >10 where the number "10" is one possibility out of the sixteen possible measurement results, as discussed above. All other reading combinations will be averaged and the condition corresponding closest to the average will be indicated.

In the facial evaluation mode, a total of eight individual skin measurements are taken. If seven or more readings fall within one category, the processor will report that category as the skin condition. The "COMBINATION" category will be reported if any of the following conditions are met:

if 4 readings are $\leq 10$ and 4 readings >10
if 3 readings are $\leq 10$ and 5 readings >10
if 5 readings are $\leq 10$ and 3 readings >10
if 6 readings are $\leq 10$ and 2 readings >10
if 2 readings are $\leq 10$ and 6 readings >10

All other readings will be averaged and the condition corresponding closest to the average will be indicated. Other criteria for selecting the skin condition to be indicated after a plurality of skin measurements have been taken may be used, the above is only one exemplary embodiment.

It should be noted that the index shown in FIG. 2a has combination categories already indicated on the scale 106. That is, DRY/NORMAL and NORMAL/OILY are shown. When such a scale is used, the COMBINATION icon 96 would not be used. Instead, the combination would be directly indicated on the scale.

If the voice switch 82 is depressed, the processor will concurrently feed a representative signal to the speaker that audibly communicates a message to the operator. The audible message substantially duplicates the visually displayed recommendation, and is adaptable to change in response to changes in the lens covers 120 as previously described.

Turning now to FIG. 8, a schematic diagram is presented showing an automated system where the processor U4 receives the temperature sensor SEN1 output and the humidity sensor SEN2 output directly and automatically performs compensation. No manual temperature switch is included. Also, a voice module socket device 154 is shown as well as a nine volt battery. Other than these changes, the diagram is approximately the same as FIG. 7. The nine volt battery as the power source is used with a voltage divider 152 to provide the correct voltage to the circuit 130.

Figure 9A:
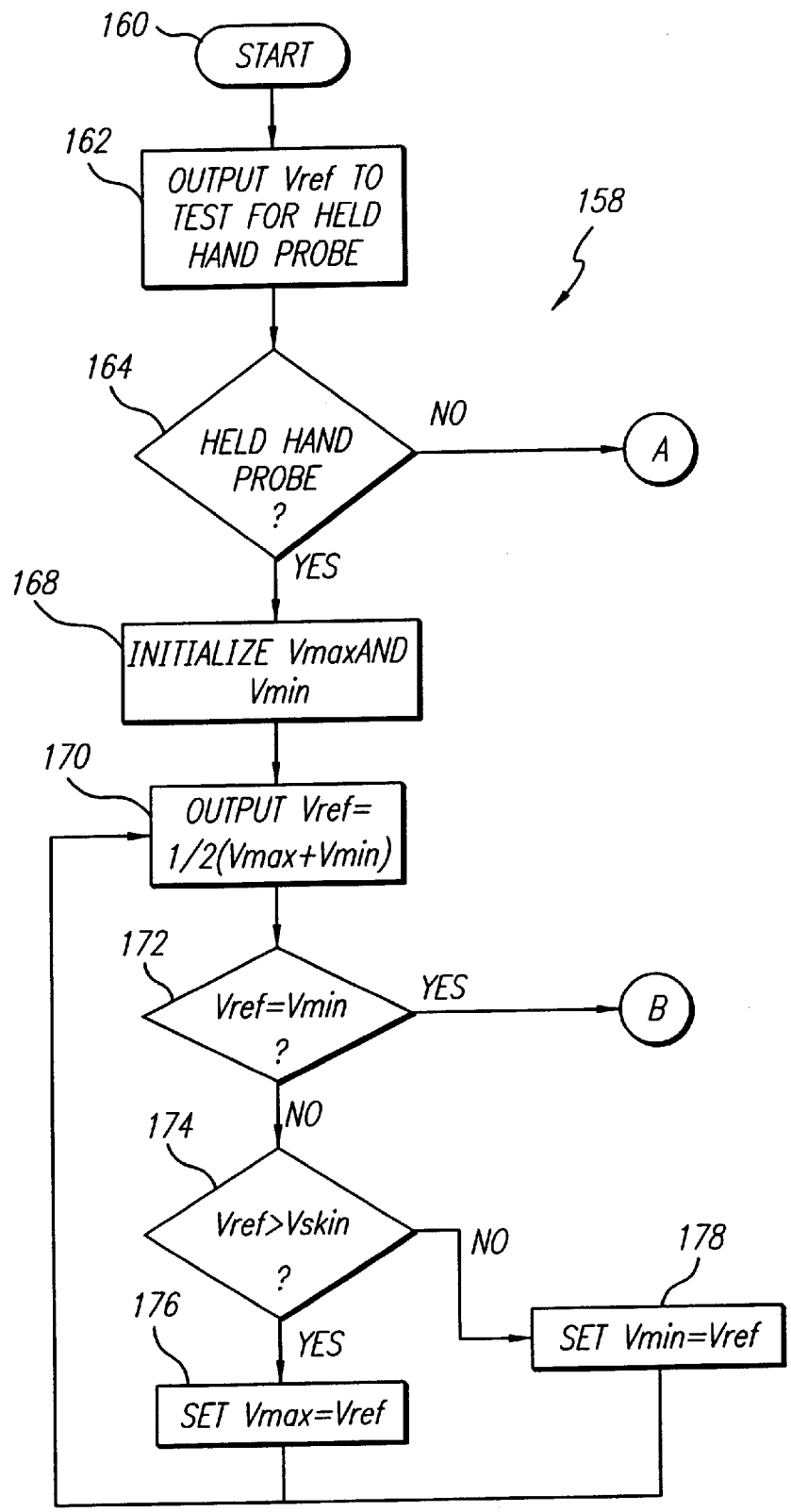
FIGS. 9a and 9b present a program for performing a skin condition measurement, including compensations for engagement of the ethnic mode and the humidity compensation mode.
Figure 9B:
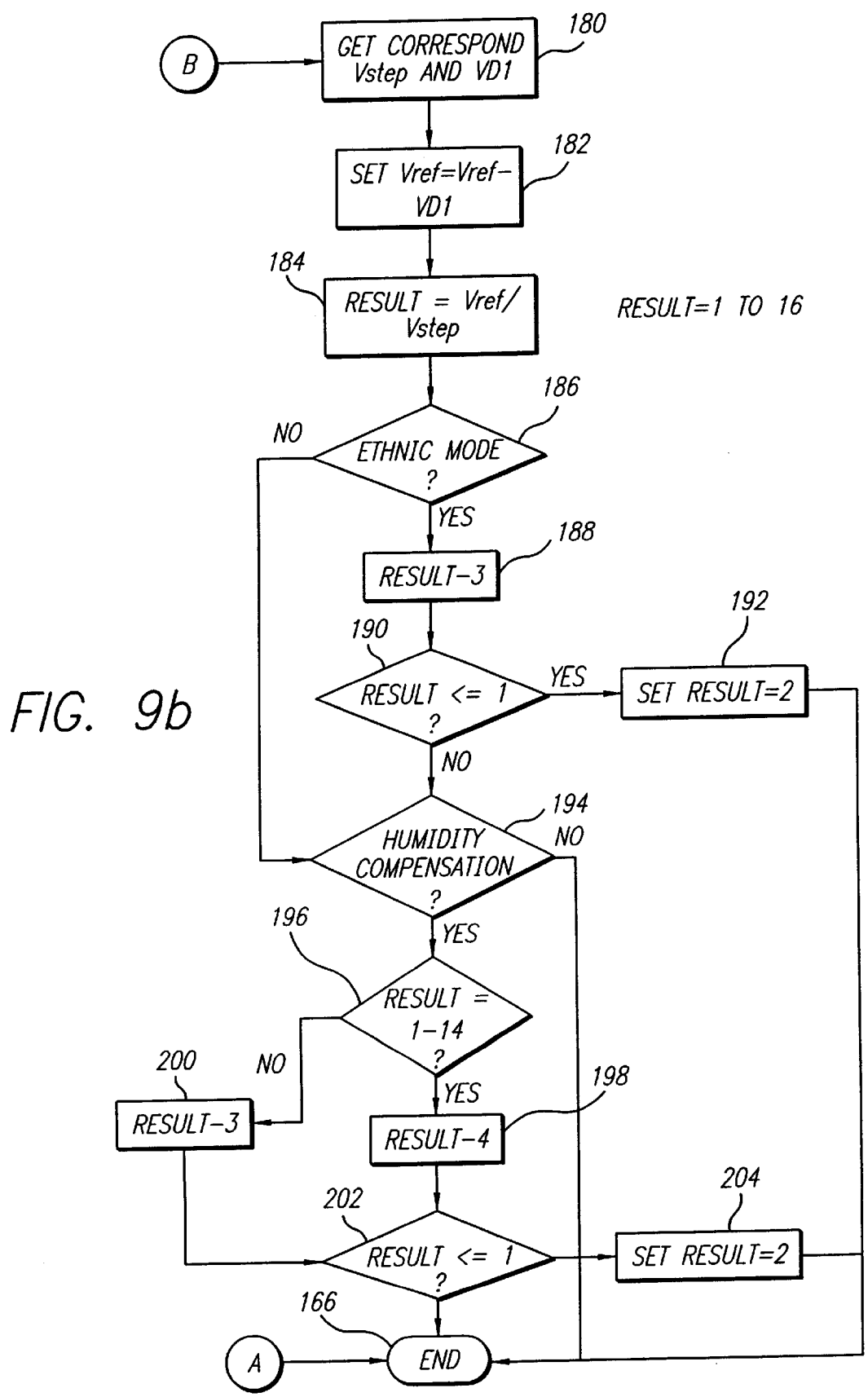

Referring now to FIGS. 9a and 9b, a program for performing a skin condition measurement is provided. The program is started 160 and the probe output voltage is tested 162 for the presence of skin contact with the probes. The voltage is analyzed 164 and If there is no skin contact, the process is ended 166. If skin contact exists, Vmax and Vmin are initialized 168. Vref is determined by halving (vmax+Vmin) 170. Vref is then compared to Vmin 172 and if they are not equal, Vref is compared to Vskin 174. If Vref is greater than Vskin, Vmax is set equal to Vref 176 and the process of halving (vmax+Vmin) 170 is repeated. However, if Vref is not greater than Vskin, Vmin is set equal to Vref and the process of halving (vmax+Vmin) 170 is begun again. In this way, the value of Vskin is finally determined at step 172.

When Vref equals Vmin 172, the corresponding Vstep and VD1 are obtained from memory. The value VD1 is the lowest value at a particular temperature that the voltage may be to indicate category one of the sixteen categories (for example, the voltage at dry level 1, hence "VD1", FIG. 3). The voltage Vstep is the difference voltage between each of the sixteen categories. These values may vary depending on the temperature One embodiment is presented below:

Degrees C VD1 Vstep
20 0.151 0.177
21 0.144 0.184
22 0.210 0.184

Thus the voltage at category 1, which is "DRY" in FIG. 2a is 0.151 volts. Level two however would be 0.151 v+0.177 v=0.328 v.

Vref is then set to Vref−VD1 182 and the result of Vref divided by Vstep is determined 184. This result is classified into one of the sixteen categories according to whichever number is closest. Results exceeding sixteen are assigned the number sixteen. It is then determined if the ethnic mode is engaged 186. If so, the result is decreased by a predetermined amount, in this case by three 188. However, if the resulting value is less than one 190, the result is set at two and the measurement is ended 166. If the result is not less than one 190, it is then determined if the humidity compensation mode is engaged 194. If it is not, then the measurement is ended 166. However, if the humidity compensation mode is engaged, the result is analyzed to determine if it is within the range of one to fourteen 196. If it is, the result is decreased by a predetermined amount, in this case by four 198. If the result is outside the range of one to fourteen, the result is decreased by a different predetermined amount, in this embodiment three 200. Either decreased result is analyzed to determine if it is less than one 202. If the result is less than one, the result is set to two 204 and the measurement ended 166. If the result is not less than one 202, the measurement is ended 166.

Figure 10:
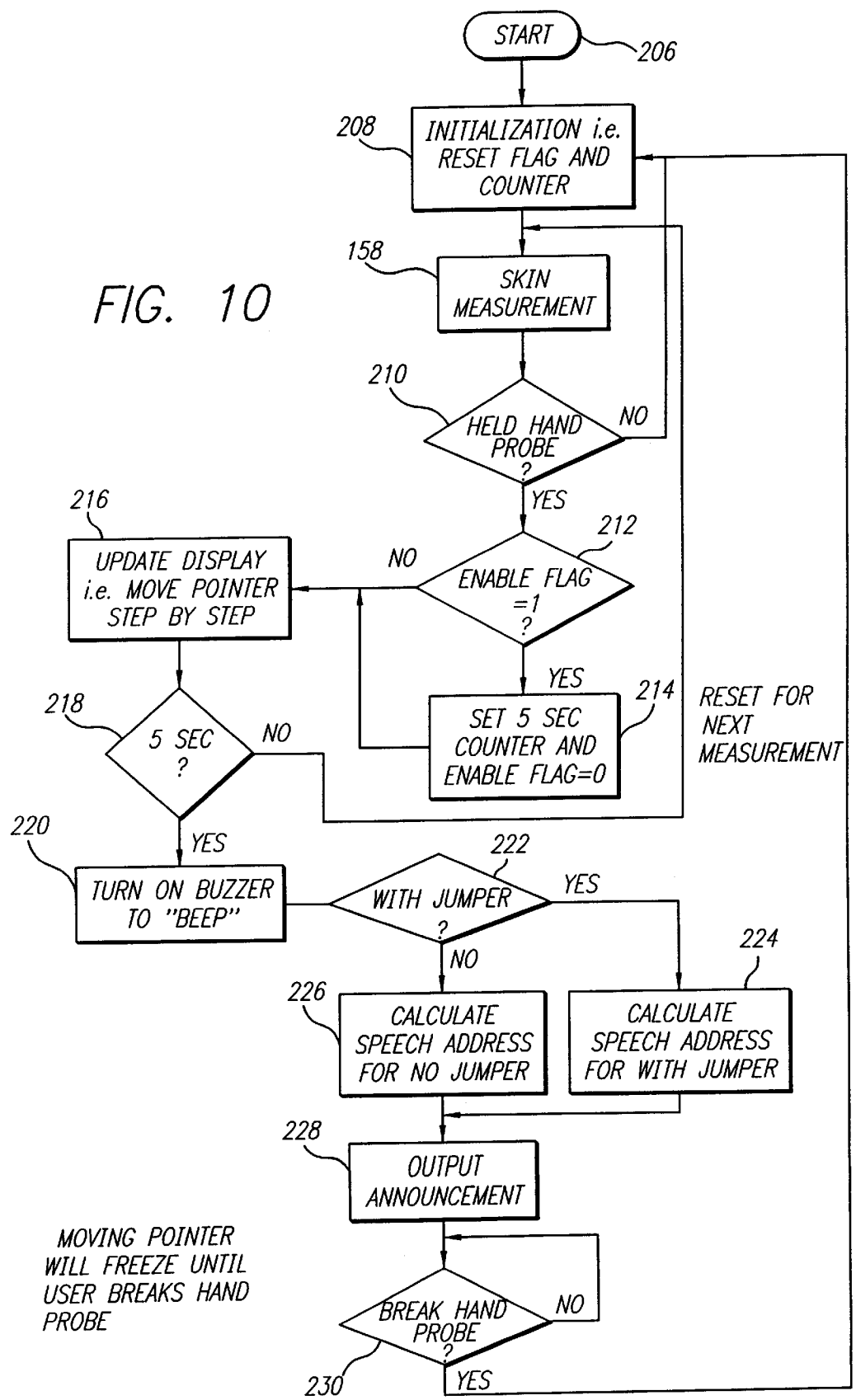
FIG. 10 presents a program for performing a random skin measurement at a single location.

Turning now to FIG. 10, a random skin measurement program is presented. After start 206, initialization occurs 208. In initialization, a flag is set to zero as well as a counter. A skin measurement is then taken 158, such as than shown in FIGS. 9a and 9b. Contact with the subject's skin is continually monitored 210 and if that contact is broken, the program returns to the initialization step 208. However, if contact with the subject's skin remains, the status of the flag is checked 212 and if the flag is equal to one, a five-second counter is set and the flag value is set to zero 214. The display is then updated to the presently determined skin condition by activating the display icons 112 sequentially, step by step from the lowest level PRY level 1 in FIG. 2a) until the skin condition result is indicated 216. Additionally, if the flag was determined to be at other than a "one" value 212, the display is also updated in the same way 216. Five seconds are counted 218 and until five seconds have elapsed, the measurement process continues.

At the end of five seconds, a signal is given 220. The program then determines which classification index is installed in the system. As mentioned above, a jumper JP1 (FIG. 7) may be used to change classification indices. If the jumper is installed 222, the speech address for the skin condition result is determined 224. If the jumper is not installed 222, a different speech address for that skin condition result is determined 226. The speech is retrieved and an audio announcement made 228. The display freezes at the indicated skin condition result until the skin contact with a probe is broken 230. The program then reverts to the initialization step 208.

Figure 11A:
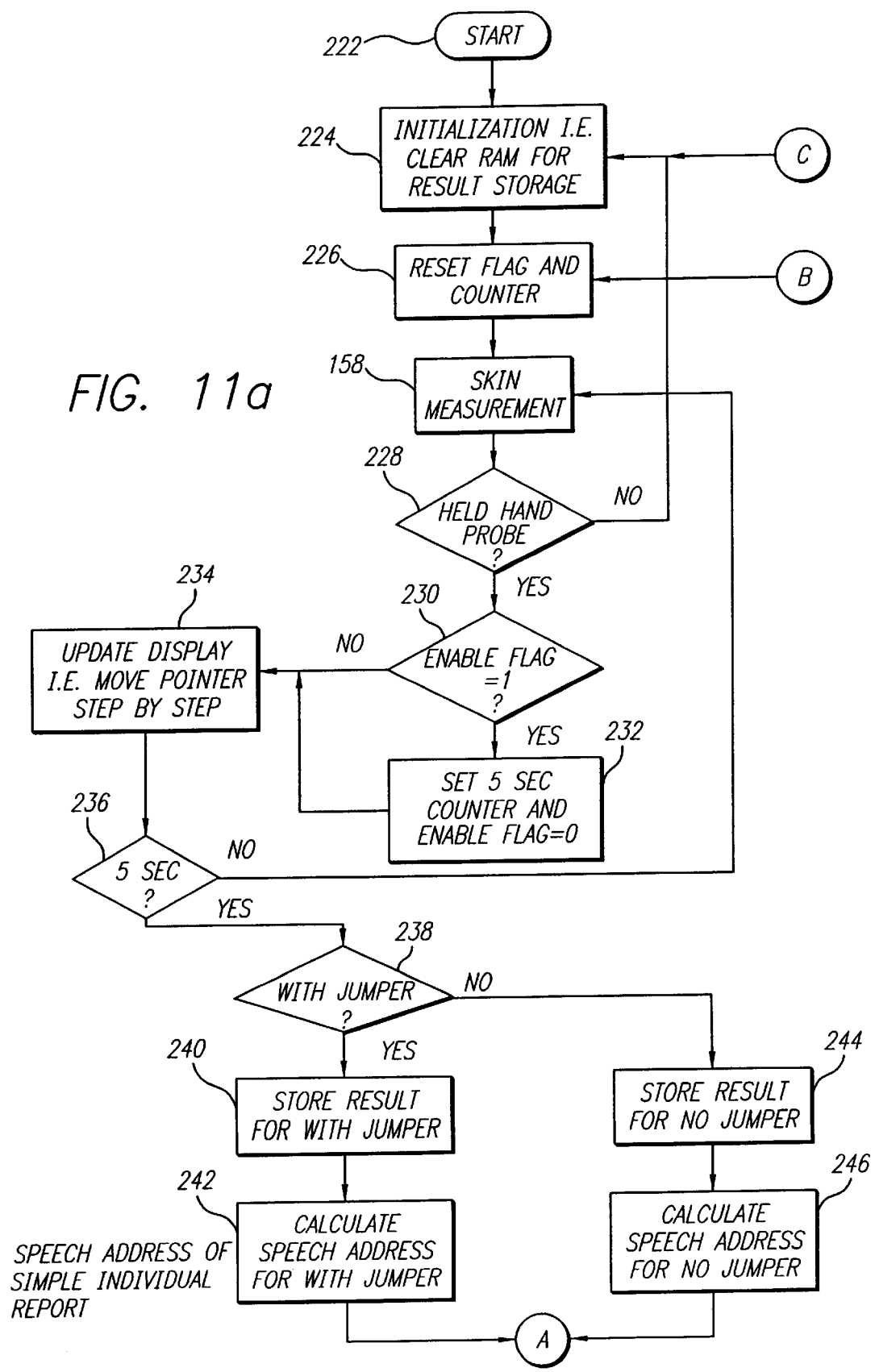
FIGS. 11a and 11b present a T-zone mode skin measurement program in which multiple skin measurements are taken before a final skin condition result is indicated.
Figure 11B:
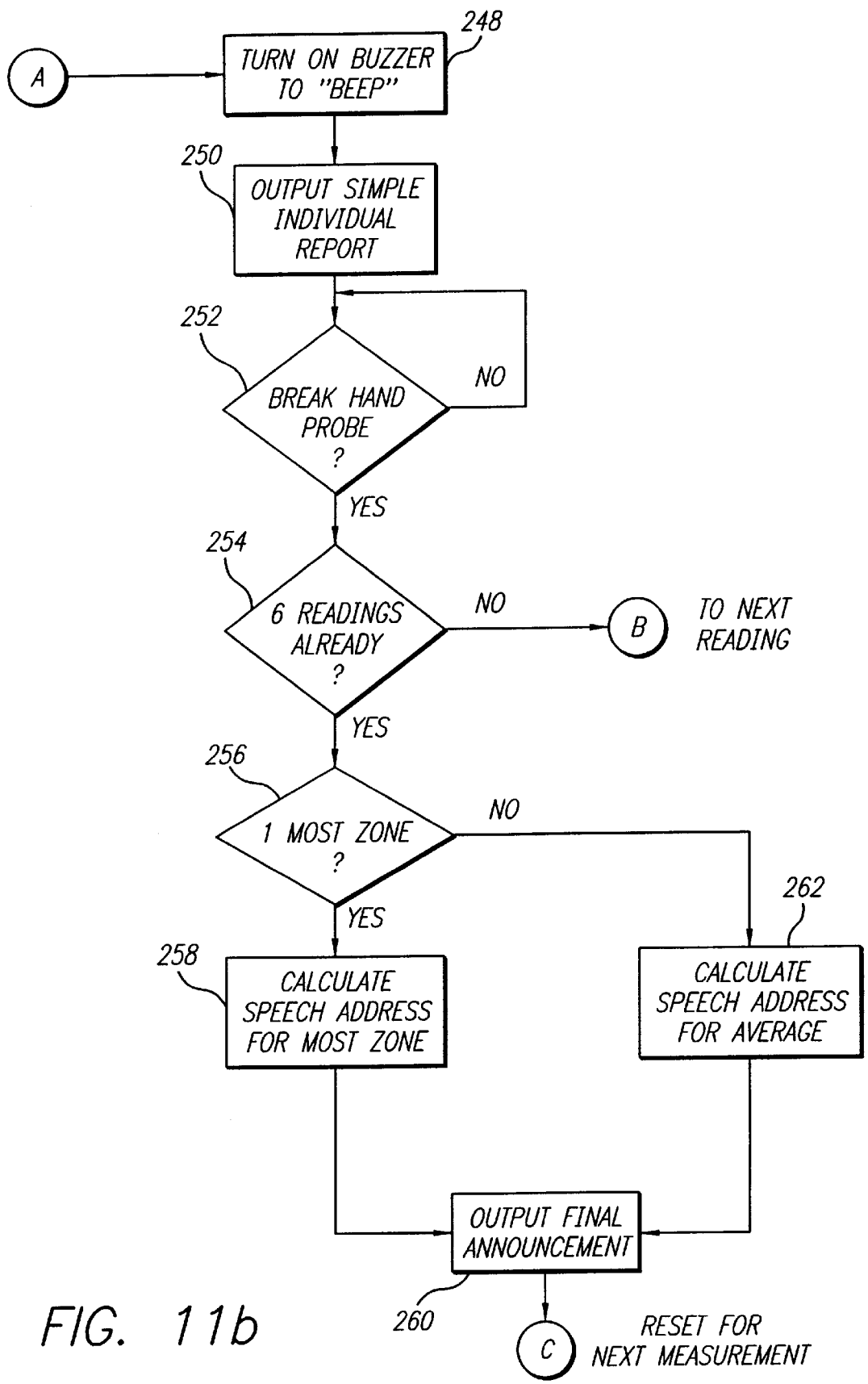

In FIGS. 11a and 11b, a multiple-measurement mode program is presented in which multiple skin measurements must be taken before a final skin condition result is presented. The example presented is a T-zone mode program. After start 222, initialization 224 occurs in which random access memory is cleared. The flag is then reset to a value of "one" and the counter is reset 226. A skin measurement 158 is conducted and, as in the random mode program, continual monitoring of skin to probe contact occurs 228. If the skin to probe contact is broken, the program returns to the reset step 226. However, if constant skin contact remains, the program proceeds to the determination of the flag status 230 and if the flag is at a value of "one", it is set to zero and a five second counter started 232. The display is then updated 234 for the skin measurement by activating the icons 112 step by step to indicate the individual measurement result. If the flag was already other than one at step 230, the display is updated 234 as described above.

If five seconds have elapsed 236, the program then determines which language has been selected 238. In the embodiment shown, it is determined if the jumper JP1 FIG. 7) has been installed. If so, the result for this individual skin measurement is stored and the address or addresses in the language device for the appropriate words, phrase, or sentence is determined 242. In the case where the other language has been selected (by virtue of the jumper not being installed), the result is stored for no jumper 244 and the address or addresses in the language device for the appropriate words, phrase, or sentence for that case is determined 246. An audible tone is issued 248 indicating measurement completion (one beep) and the audible output in the selected language is provided for that single measurement. The program then waits for the probe or probes to break contact with the skin 252 indicating that a probe has been moved to a new skin location. If six readings have not yet been taken 254, the program returns to the reset step 226 and begins a new measurement. If six readings have already been taken 254, the program determines the final skin condition result from the six readings 256. In this embodiment, the program determines if most readings fell within one category 256. If so, then the address for the words, phrase, or sentence is determined and the audible announcement of that skin condition made 260. If most readings do not fall within one category, an average is taken and the address for the words, phrase, or sentence is determined and the audible announcement of that skin condition made 260. The program then returns to the initialization step 224 for the next skin condition measurement process.

The facial evaluation mode would use a program similar to the T-zone mode program with the number of individual skin measurements used to determine the final result changed from six to eight.

Those skilled in the art will appreciate the added convenience of providing a customized audio output that allows the operator of the analyzer to concentrate on applying the probe safely to different positions on the face without having to rely solely on a visual display. Such feature is especially important during multiple measurements of the skin where diligence is important in making a substantially contemporaneous overall evaluation of skin condition.

The capability of making such composite or multiple measurements will also be appreciated since operators of the skin analyzer of the present invention will be free from the burden of manually calculating several measurement results to arrive at an overall skin condition. Those skilled in the art will recognize the applicability and usefulness of the T-zone and facial evaluation modes as these are often widely recognized as accepted composite skin condition measurement locations of the face.

Furthermore, the replaceability of language modules will also be appreciated in the art for several reasons. The first is that multi-language functionality allows widespread use of the analyzer in countries where multiple languages are commonly used. This feature increases the market for operators of the analyzer. Secondly, providing an interchangeable language device substantially reduces the cost of manufacture of the analyzers since worldwide production of the analyzers may be realized at a central fabrication facility. Units destined for different countries need only be modified by a simple language device replacement.

While particular forms of the invention have been illustrated and described, it will be apparent to those familiar with the art that various modifications and improvements can be made without departing from the scope of the invention as defined by the following claims.

What is claimed is:

1. Apparatus for measuring a condition of skin, comprising:

a probe apparatus that provides an output probe signal in response to contact with skin, said probe signal being representative of a skin characteristic;

a memory in which are stored multiple threshold levels;

a language memory in which are stored words in a first language that are descriptive of skin conditions;

an environmental sensor located at a position that is not in contact with the skin that senses an environmental component and provides an environmental sensor signal representative of the environmental component sensed;

a processor that:
  receives the output probe signal;
  retrieves the multiple threshold levels from the memory;
  compares the output probe signal to said multiple threshold levels; and
  provides a skin condition signal based on said comparison;
a display that presents the environmental component sensed as represented by the environmental sensor signal: and
a voice output device that receives the skin condition signal and provides an audible representation of said signal in the first language.

2. The apparatus for measuring a condition of skin of claim 1 further comprising:
  a second language memory in which are stored words in a second language that are descriptive of skin conditions;
  a language selection switch, the actuation of which selects the second language memory;
  wherein the voice output device provides the audible representation of said skin condition signal in the second language in response to actuation of the language selection switch.

3. The apparatus for measuring the condition of skin of claim 1
  wherein the processor responds to the environmental sensor signal to adjust the skin condition signal according to the environmental sensor signal.

4. The apparatus for measuring the condition of skin of claim 3 wherein the environmental sensor comprises an humidity sensor that provides an humidity sense signal;
  wherein the processor responds to the humidity signal and adjusts the skin condition signal if the humidity signal indicates a sensed humidity exceeding a predetermined threshold.

5. The apparatus for measuring a condition of skin of claim 1 wherein the environmental sensor comprises a temperature sensor that provides a temperature sense signal;
  wherein the processor responds to the temperature signal and adjusts the skin condition signal in accordance with the temperature indicated by the temperature sense signal.

6. The apparatus for measuring a condition of skin of claim 1 further comprising:
  a composite measuring mode switch, the actuation of which selects a composite measuring mode;
  wherein the processor:
    in response to the selection of a composite measuring mode, provides a prompt to move the probe apparatus to a second location on the skin for producing a second output probe signal;
    retrieves the multiple threshold levels from the memory;
    compares a plurality of output probe signals to said multiple threshold levels; and
    provides the skin condition signal based on said plurality of comparisons.

7. The apparatus for measuring a condition of skin of claim 1 further comprising:
  a power source connected to supply power to the measuring apparatus;
  wherein the processor automatically monitors for output probe signals and if no output probe signal is received within a predetermined time period, the processor automatically interrupts the power from said power source.

8. The apparatus for measuring the skin condition of claim 1 further comprising:
  a skin type selection switch that provides a skin type signal when actuated;
  wherein the processor adjusts the skin condition signal by a predetermined factor in response to the skin type signal.

9. The apparatus for measuring a condition of skin of claim 1 wherein:
  the display comprises a visual display that receives the skin condition signal and provides a visual representation of said signal;
  a first display scale mounted adjacent the display providing a plurality of categories defining the skin condition signal;
  a second display scale interchangeable with the first display scale having a different plurality of categories;
  a classification device, the actuation of which selects a first classification according to the first display scale or a second classification according to the second display scale;
  wherein the processor provides the skin condition signal according to the particular actuation of the classification device.

10. Apparatus for measuring a condition of skin, comprising:
  a probe apparatus that provides an output probe signal in response to contact with skin, said probe signal being representative of a skin characteristic;
  a memory in which are stored multiple threshold levels;
  a language memory in which are stored words in a first language that are descriptive of skin conditions;
  a second language memory in which are stored words in a second language that are descriptive of skin conditions;
  a processor that:
    receives the output probe signal;
    retrieves the multiple threshold levels from the memory;
    compares the output probe signal to said multiple threshold levels; and
    provides a skin condition signal based on said comparison;
  a voice output device that receives the skin condition signal and provides an audible representation of said signal in the first language;
  a language selection switch, the actuation of which selects the second language memory;
  wherein the voice output device provides the audible representation of said skin condition signal in the second language in response to actuation of the language selection switch;
  a portable housing in which are mounted the memory, the processor, and the voice output device;
  a removable language device comprising the second language memory, said device having accessible electrical contacts for establishing communications with the second language memory; and
  a mounting device disposed in the portable housing configured to accept, retain in a predetermined position, and electrically connect to the accessible electrical contacts of the language device, said mounting device configured so that the language device may be removed and replaced with another language device.

11. Apparatus for measuring a condition of skin, comprising:
   a probe apparatus that provides an output probe signal in response to contact with skin at a particular location, said probe signal being representative of a skin characteristic;
   a memory in which are stored multiple threshold levels;
   a processor that:
      receives the output probe signal;
      provides a prompt to move the probe apparatus to a second location on the skin for producing a second output probe signal;
      retrieves the multiple threshold levels from the memory;
      compares the plurality of output probe signals to said multiple threshold levels; and
      provides a skin condition signal based on said plurality of comparisons;
   an output device that presents the skin condition signal in a human perceptible form.

12. The apparatus for measuring the condition of skin of claim 11 further comprising:
   an environmental sensor that provides an environmental sensor signal representative of the environmental component sensed;
   wherein the processor responds to the environmental sensor signal to adjust the skin condition signal according to the environmental sensor signal.

13. The apparatus for measuring the condition of skin of claim 12 wherein the environmental sensor comprises an humidity sensor that provides an humidity sense signal;
   wherein the processor responds to the humidity signal and adjusts the skin condition signal if the humidity signal indicates a sensed humidity exceeding a predetermined threshold.

14. The apparatus for measuring a condition of skin of claim 13 wherein the environmental sensor comprises a temperature sensor that provides a temperature sense signal;
   wherein the processor responds to the temperature signal and adjusts the skin condition signal in accordance with the temperature indicated by the temperature sense signal.

15. The apparatus for measuring a condition of skin of claim 14 further comprising:
   a display;
   wherein the processor provides signals to the display for the display of the sensed temperature and the sensed humidity.

16. The apparatus for measuring a condition of skin of claim 11 further comprising:
   a power source connected to supply power to the measuring apparatus;
   wherein the processor automatically monitors for output probe signals and if no output probe signal is received within a predetermined time period, the processor automatically interrupts the power from said power source.

17. The apparatus for measuring the skin condition of claim 11 further comprising:
   a skin type selection switch that provides a skin type signal when actuated;
   wherein the processor adjusts the skin condition signal by a predetermined factor in response to the skin type signal.

18. The apparatus for measuring a condition of skin of claim 11 further comprising:
   a visual display that receives the skin condition signal and provides a visual representation of said signal;
   a first display scale mounted adjacent the display providing a plurality of categories defining the skin condition signal;
   a second display scale interchangeable with the first display scale having a different plurality of categories;
   a classification device, the actuation of which selects a first classification according to the first display scale or a second classification according to the second display scale;
   wherein the processor provides the skin condition signal according to the particular actuation of the classification device.

19. The apparatus for measuring a condition of skin of claim 11 further comprising:
   a language memory in which are stored words in a first language that are descriptive of skin conditions; and
   a voice output device that receives the skin condition signal and provides an audible representation of said signal in the first language.

20. The apparatus for measuring a condition of skin of claim 19 further comprising:
   a second language memory in which are stored words in a second language that are descriptive of skin conditions;
   a language selection switch, the actuation of which selects the second language memory;
   wherein the voice output device provides the audible representation of said skin condition signal in the second language in response to actuation of the language selection switch.

21. The apparatus for measuring a condition of skin of claim 20 further comprising:
   a portable housing in which is mounted the memory, the processor, and the voice output device;
   a removable language device comprising the second language memory, said device having accessible electrical contacts for establishing communications with the second language memory; and
   a mounting device disposed in the portable housing configured to accept, retain in a predetermined position, and electrically connect to the accessible electrical contacts of the language device, said mounting device configured so that the language device may be removed and replaced with another language device.

22. A method of measuring a condition of skin, the method comprising the steps of:
   applying a probe apparatus to a first location of the skin to be measured, the probe apparatus providing a first output probe signal representative of a skin characteristic in response to said application to the skin;
   storing the first output probe signal;
   moving the probe apparatus to a second location on the skin and producing a second output probe signal;
   storing the second output probe signal;
   comparing the plurality of stored output probe signals to multiple threshold levels; and
   providing a skin condition signal based on said plurality of comparisons.

23. The method of measuring a condition of skin according to claim 22 comprising the further steps of:

measuring a component of the environment;

adjusting the skin condition signal according to the measured environmental component; and displaying the measured environmental component.

24. The method of measuring a condition of skin according to claim 22 comprising the further step of:

audibly announcing the skin condition in one of a plurality of selectable languages.

25. The method of measuring a condition of skin according to claim 22 comprising the further step of:

visually displaying the measured skin condition;

mounting a first display scale adjacent the display, said first display scale having a plurality of categories that define the skin condition signal;

interchanging the first display scale with a second display scale, said second display scale having a different plurality of categories for defining the skin condition signal;

selecting between a first and second classification according to the first and second display scales whereby the skin condition signal is displayed according to the classification selected.

* * * * *